United States Patent [19]

Jonsson et al.

[11] Patent Number: 4,784,495

[45] Date of Patent: Nov. 15, 1988

[54] SYSTEM FOR PREPARING A FLUID INTENDED FOR A MEDICAL PROCEDURE BY MIXING AT LEAST ONE CONCENTRATE IN POWDER FORM WITH WATER

[75] Inventors: Lennart U. P. Jonsson, Furulund; Per-Olov A. V. Carlsson, Sosdala; Dan Jonsson, Lund; Sven Jonsson, Staffanstorp; Stefan L. Knutsson, Bjarred; Ragnar Tryggvason, Loddekopinge, all of Sweden

[73] Assignee: Gambro AB, Sweden

[21] Appl. No.: 130,879

[22] Filed: Dec. 10, 1987

[30] Foreign Application Priority Data

Feb. 6, 1987 [SE] Sweden .................. 8700461
May 27, 1987 [SE] Sweden .................. 8702234
Aug. 11, 1987 [SE] Sweden .................. 8703120
Sep. 18, 1987 [SE] Sweden .................. 8703626

[51] Int. Cl.$^4$ ............................ B01F 15/04
[52] U.S. Cl. ........................ 366/151; 137/88; 366/160
[58] Field of Search ............. 366/150, 151, 159, 160, 366/161, 162, 163, 166, 16, 17, 19, 21, 140, 142; 137/88, 98, 92, 93

[56] References Cited

U.S. PATENT DOCUMENTS

| | | |
|---|---|---|
| 3,560,380 | 2/1971 | Stade . |
| 3,653,640 | 4/1972 | Hendrik .............. 366/151 |
| 3,843,099 | 10/1974 | Duncan ................ 137/88 |
| 4,158,034 | 6/1979 | Riede et al. .......... 134/22.12 |
| 4,357,953 | 11/1982 | Patterson ............. 137/88 |
| 4,404,192 | 9/1983 | Suzuki . |
| 4,494,209 | 1/1985 | Agarwal .............. 137/88 |
| 4,621,927 | 11/1986 | Hiroi ................. 366/151 |
| 4,688,946 | 8/1987 | Latif ................. 366/151 |

FOREIGN PATENT DOCUMENTS

| | | |
|---|---|---|
| 0034916 | 9/1981 | European Pat. Off. . |
| 0022922 | 5/1983 | European Pat. Off. . |
| 0177614 | 4/1986 | European Pat. Off. . |
| WO85/03435 | 8/1985 | PCT Int'l Appl. . |
| WO86/03416 | 6/1986 | PCT Int'l Appl. . |
| WO86/03417 | 6/1986 | PCT Int'l Appl. . |
| 164770 | 9/1958 | Sweden . |

Primary Examiner—Robert W. Jenkins
Attorney, Agent, or Firm—Lerner, David, Littenberg, Krumholz & Mentlik

[57] ABSTRACT

A system for preparing a fluid intended for a medical procedure substantially at the time of use by mixing of at least one concentrate in powder form with water. The system includes a reservoir for a source of water, at least one vessel containing a concentrate in powder form and a concentrate fluid circuit for withdrawing a small quantity of water from the reservoir and passing same through the vessel containing the concentrate in powder form in order to dissolve the concentrate to produce a concentrate fluid, and for then conducting the concentrate fluid to a primary fluid circuit communicating with the reservoir so that the produced concentrate fluid is mixed with the rest of the water withdrawn from the reservoir. In a preferred embodiment, the vessel comprises a self-contained cartridge containing a quantity of concentrate in powder form therein which is suitable for one treatment procedure. The system is intended in particular for the preparation of fluids for use in connection with medical procedures such as hemodialysis, hemodiafiltration and hemofiltration. However, it may also be used for the preparation of fluids for other medical procedures or treatments as well.

110 Claims, 8 Drawing Sheets

SYSTEM FOR PREPARING A FLUID INTENDED FOR A MEDICAL PROCEDURE BY MIXING AT LEAST ONE CONCENTRATE IN POWDER FORM WITH WATER

FIELD OF THE INVENTION

The present invention relates to a system for preparing a fluid intended for a medical procedure and, more particularly, to a system for preparing such a fluid by mixing of at least one concentrate in powder form with water. The system of the present invention is intended, in particular, for the preparation of fluids for use in connection with medical procedures such as hemodialysis, hemodiafiltration and hemofiltration. For instance, the system of the present invention may be used in connection with the preparation of a dialysis fluid for use in connection with hemodialysis, as well as used for preparation of replacement fluids used in connection with hemofiltration or hemodiafiltration. To those skilled in the art, it will be apparent moreover that the system of the present invention can be used in connection with other medical procedures or treatment where a fluid suitable for the treatment is obtained from mixing of water with at least one concentrate in powder form, such as, for example, the production of flushing fluids for cleaning of wounds and the like.

BACKGROUND OF THE INVENTION

In hemodialysis operations, the blood of a patient suffering from impaired kidney function is conducted along one side of a permeable membrane in a dialyzer device, at the same time as dialysis fluid is conducted along the opposite side of the same membrane. The poisons or other waste substances that are to be removed from the blood pass with the help of diffusion from the blood of the patient to the dialysis fluid through the permeable membrane. Normally, a certain amount of fluid, primarily water, is also withdrawn from the blood so as to bring about a lowering of the weight of the patient.

Hemodiafiltration differs from hemodialysis first and foremost in that a more permeable filter membrane is utilized, Consequently, greater ultrafiltration or withdrawal of fluid from the body is obtained, which makes it necessary for a part of the ultrafiltrate removed to be replaced by a replacement fluid. Hemofiltration differs from hemodialysis and hemodiafiltration in that no dialysis fluid is utilized on the opposite side of the permeable membrane along which the blood is conducted. Instead, with the help of a filter, a large quantity of ultrafiltrate is withdrawn from the blood across the filter membrane, which has to be replaced at least partly by a corresponding quantity of replacement fluid.

Different types of control systems are normally used for hemodialysis, hemodiafiltration and hemofiltration operations, respectively. However, they all have in common that at least one concentrate fluid is mixed with pure water in order to produce either the dialysis fluid in connection with hemodialysis operations, or the replacement fluids in connection with hemodiafiltration and hemofiltration operations. Normally, the concentrate to be mixed with water is prepared in centralized preparation plants and is then transferred to the point of treatment in large kegs or other containers. Alternatively, the concentrate may be prepared directly on the spot in large tanks or the like before the treatment is to be started. Thus, in either instance, the concentrate to be used in the medical treatment is prepared in the form of a solution prior to actual use in connection with the medical treatment. At the time of treatment, the concentrate soultion is then mixed with water to provide the desired prepared solution for the particular medical treatment.

Examples of previously used concentrates, in either powder or liquid form, for use in preparing such prior art concentrate solutions may be found, for instance, in U.S. Pat. Nos. 3,560,380; 4,404,192; European Patent Specification Ep-B1-0 022 922; Eurpean Patent Application Nos. EP-A1-0 034 916; EP-A1-0 177 614; and PCT Publication No. WO85/03435. Further, U.S. Pat. No. 4,158,034 describes an example of how such concentrate solutions prepared beforehand can be used in the preparation of a solution suitable for dialysis operations.

Major problems can arise with such prior art types of concentrate solutions prepared prior to their utilization in connection with medical procedures due to the fact that certain concentrates do not always remain stable and/or bacteria-free if prepared in large quantities beforehand. For instance, precipitation may occur either during the transport of concentrate solutions from centralized preparation plants, or even in the aforementioned large tanks or the like before actual treatment is to begin. Furthermore, preparation of concentrate solutions before actual usage in connection with medical treatment can result in bacteria growth if allowed to stand for substantial periods of time.

SUMMARY OF THE INVENTION

The present invention is directed to a system which overcomes or minimizes the aforementioned difficulties and problems of the prior art by providing a system for preparing a fluid intended for a medical procedure substantially at the time of use by mixing of at least one concentrate in powder form with water. More particularly, the system of the present invention includes a source of water such as a reservoir, at least one vessel for containing a concentrate in powder form, and a concentrate fluid circuit for withdrawing a small quantity of water from the source of water and passing same through the vessel containing the concentrate in powder form in order to dissolve the concentrate to produce a concentrate fluid, and for then conducting the concentrate fluid to a primary fluid circuit to be mixed with the rest of the water withdrawn from the source of water.

More particulary, in accordance with one aspect of the present invention, primary or first fluid conducting means is provided having one end communicating with the source of water for withdrawing water from the source and a second end for delivering a prepared solution. The concentrate fluid circuit includes second fluid conducting means which communicates with the source of water and with an inlet to the vessel containing the concentrate in powder form for introducing water from the source of water into the vessel to produce a concentrate fluid containing dissolved powder concentrate and water, and third fluid conducting means which communicates with the outlet of the vessel and with a mixing point in the first fluid conducting means intermediate the first and second ends thereof for conducting the produced concentrate fluid from the vessel into the first fluid conducting means to be mixed with water being conducted therethrough, to thereby produce the prepared solution for delivery to the second end of the first fluid conducting means. Measuring means are provided in the first fluid conducting means downstream of the mixing point for measuring the composition of prepared solution obtained by mixing of the produced concentrate fluid and water being conducted through the first fluid conducting means, and flow regulating means are provided in the third fluid conducting means which is responsive to the measuring means for controlling the flow of concentrate fluid from the vessel.

In accordance with another aspect of the present invention, the system also includes a source of second concentrate fluid, and fourth fluid conducting means having a first end communicating with the source of second concentrate fluid and a second end communicating with the primary or first fluid conducting means at a second mixing point intermediate the first and second ends thereof for introducing the second concentrate fluid into the primary fluid conducting means to be mixed with fluid being conducted therethrough to produce the prepared solution downstream of the first and second mixing points, the prepared solution thus being comprised of first concentrate fluid produced by conducting water from the source of water into the vessel containing the concentrate in powder form and second concentrate fluid from the source thereof, both of which are mixed with water withdrawn from the source of water through the primary fluid conducting means.

In accordance with a still further aspect of the present invention, the system includes first and second vessels each containing a concentrate in powder form, the two concentrates being different from one another. The two vessels are adapted to be connected in the concentrate fluid circuit through the use of first and second connection means. The first connection means is provided at a first location in the concentrate fluid circuit for connecting the first vessel to the concentrate fluid circuit so as to introduce fluid containing water from the source of water into the first vessel to dissolve the first concentrate therein and to withdraw the dissolved first concentrate therefrom, and the second connection means is provided at a second location in the concentrate fluid circuit for connecting the second vessel to the concentrate fluid circuit so as to introduce fluid containing water from the source of water into the second vessel to dissolve the second concentrate and to withdraw fluid containing the dissolved second concentrate from the second vessel. The first and second connection means are different from one another so that the first vessel is only connectable by the first connection means to the concentrate fluid circuit at the first location, and the second vessel is only connectable by the second connection means to the concentrate fluid circuit at the second location. Conveniently, in accordance with a preferred embodiment, the first and second connection means comprise first and second holders, with the first holder being configured to only hold a vessel having the configuration of the first vessel, and the second holder being configured to only hold a vessel having the configuration of the second vessel.

In accordance with another aspect of the present invention, the vessel containing the concentrate in powder form includes an inlet at the top thereof and an outlet at the bottom thereof, with the vessel being arranged in the concentrate fluid circuit so that water withdrawn from the source of water is introduced into the top of the vessel to produce a concentrate fluid containing dissolved powder concentrate, and so that the produced concentrate fluid is withdrawn from the bottom of the vessel and conducted to the primary fluid conducting means to be mixed with water being conducted therethrough to produce the prepared solution. In this manner, water is conducted through the vessel from the top thereof to the bottom thereof to thereby maintain and provide a relatively constant concentration level of dissolved powder concentrate being introduced into the primary fluid conducting means.

With the system of the present invention, the solution or fluid for the medical treatment can thus be prepared directly at the point of treatment and substantially at or just prior to treatment beginning. Such a system in accordance with the present invention thus avoids the necessity of preparing large quantities of concentrate solutions in liquid form, which would otherwise result in some of the concomitant problems mentioned hereinabove.

BRIEF DESCRIPTION OF THE DRAWINGS

The present invention can be more fully appreciated with reference to the following detailed description, which refers to the attached drawings in which.

DESCRIPTION OF THE PREFERRED EMBODIMENTS

Figure 1:
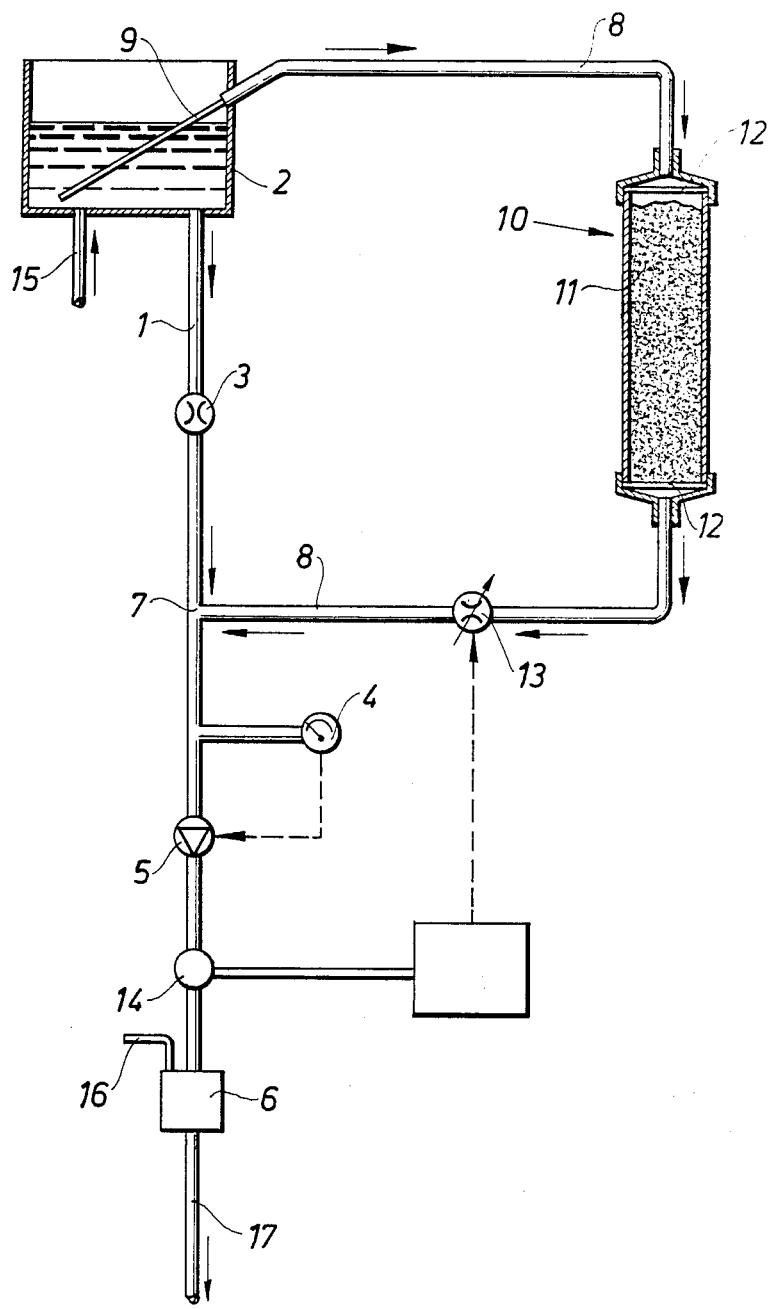
FIGS. 1-4 illustrate four alternative embodiments of the system in accordance with the present invention for preparing a fluid for a medical procedure by mixing of a concentrate in powder form with water.

Referring now to the drawings, wherein like reference characters represent like elements, there is shown various alternative arrangements for systems in accordance with the present invention for preparing a fluid for a medical procedure by mixing of at least one concentrate in powder form with water. As the system of the present invention is intended, in particular, for the preparation of dialysis fluids for hemodialysis operations, the system will be described mainly with reference to such an operation. However, it will be appreciated by those skilled in the art that, with minor modifications, the system of the present invention may also be used for the preparation of replacement fluids used in connection with hemofiltration and/or hemodiafiltration operations was well. Still further, to those skilled in the art, it will be apparent that the system in accordance with the present invention can also be used in connection with other medical treatments or procedures.

In connection with hemodialysis operations, the dialysis fluid in accordance with the present invention (as well as replacement fluids for hemodiafiltration and hemofiltration operations) typically may comprise a purified solution containing bicarbonate, such as sodium bicarbonate, together with salt compound such as sodium chloride or, optionally, other alkali or other alkali earth chlorides. With such dialysis solutions containing bicarbonate, there is a risk of precipitation of the bicarbonate, particularly in such instances where the dialysis fluid with bicarbonate is prepared at central processing plants or in large quantities at a treatment facility. The system in accordance with the present invention minimizes such problems of precipitation and/or risk of bacteria growth by preparing the fluid for medical treatment by mixing of at least one concentrate in powder form with water substantially at the time of treatment.

Referring now to FIG. 1, there is shown one arrangement for the system in accordance with the present invention in which there is provided a primary fluid conduit or duct 1 which originates from a suitable source of water, such as a liquid reservoir 2. As is known, the liquid reservoir 2 includes an inlet 15 for introduction of pure water thereinto, for example, from a reverse osmosis unit. The main conduit 1 is provided with a throttling mechanism or device 3, a pressure gauge 4, a pump 5 and a deaerating device 6. The deaeration device 6 typically is provided with an air outlet 16. This outlet may be in direct communication with the atmosphere, but, preferably, is in communication with a discharge via a suction pump (not shown). The main duct 1 includes an outlet 17 for the prepared solution obtained in the manner described more fully hereinbelow. The outlet 17 for the prepared solution, may, for example, be passed directly to one side of a dialyzer unit.

The arrangement thus far described, including the components thereof, is well-known in prior art systems for mixing of purified water with a previously prepared light concentrate to prepare a fluid for a medical procedure or treatment. Typically, in such prior art systems, the previously prepared liquid concentrate is introduced into the main conduit leading from the reservoir at a point upstream of the pump therein so that the pump will draw liquid concentrate from its source. This, for example, is shown in the system disclosed in U.S. Pat. No. 4,158,034 which is hereby incorporated by reference.

In accordance with the present invention, the system also includes a concentrate fluid circuit which, for example, may be comprised of a fluid conduit or duct 8 which originates at one end from the liquid reservoir 2, such as by means of a suction nozzle 9 which has been inserted thereinto. The other end of the concentrate fluid duct 8 joins the main fluid line 1 at a mixing point 7 which is intermediate the reservoir 2 and the outlet end 17 of the main line 1. The concentrate fluid conduit 8 includes therein a column or vessel 10 which contains a concentrate 11 in powder form arranged between two particle filters 12. In operation, a portion of the water in the reservoir 2 is drawn off through the concentrate fluid circuit 8 and is introduced into the top of the column or vessel 10 to be conducted downwardly toward the bottom thereof. The concentrate line 8 and column 10 are suitably dimensioned in such a manner that as the water drawn into the concentrate fluid circuit 8 is conducted downwardly through the column 10, a substantially saturated solution of the powder concentrate in water is obtained, to thus produce a concentrate fluid which is then conducted from the column 10 and introduced into the main line 1 at mixing point 7. In this regard, a flow regulating device 13 is provided in the portion of the concentrate fliud conduit 8 intermediate the column 10 and mixing point 7 for controlling the flow of the produced concentrate solution from the column 10 into the main line 1. A conductivity meter or other measuring device 14 is provided in the main line 1 downstream of the mixing point 7 for monitoring the composition of the prepared solution and for then controlling the flow regulating device 13. In this manner, it is possible to accurately control the ultimate mixture of produced fluid concentrate with the water being conducted from the reservoir 2 through the main line 1, even if the concentrate in powder form were to dissolve to different extents or degrees of saturation by virtue of the water being conducted through the concentrate fluid circuit 8. Instead of a conductivity measurement, the measuring device 14 could measure a different property or parameter, such as temperature, pH, or even some other parameter.

The flow regulating device 13 may conveniently comprise a simple adjustable throttling device as shown in FIG. 1. This is advantageous in that it results in a simple overall design for the system since a single pump 5 can be employed for withdrawing water from the reservoir for both the main flow through line 1 and for production of the concentrate fluid in fluid conduit 8. Specifically, by arranging the pump 5 for the suction of water in the main line 1 downstream of the mixing point 7, the pump 5 serves to withdraw water from the reservoir 2 partly through the main line 1, and partly indirectly from the same source via the concentrate fluid circuit 8. Further, with the throttling device 3 provided in the main line 1 between the source of water and the mixing point 7, and the deaerator device 6 is located in the main duct downstream of the pump 5, as shown in FIG. 1, the same pump 5 can also be used for deaeration of the prepared fluid. For the preparation of dialysis fluids, the pump 5 is operative to handle flow rates up to at least 500 ml/min, and more preferably, up to approximately 1,000 ml/min, in the main line 1 downstream of mixing point 7, whereas the flow regulating means 13 is operative to handle flow rates up to approximately 40 ml/min and, in any event, at least 30 ml/min at flow rates or approximately 1,000 ml/min in the main line 1.

Figure 2:
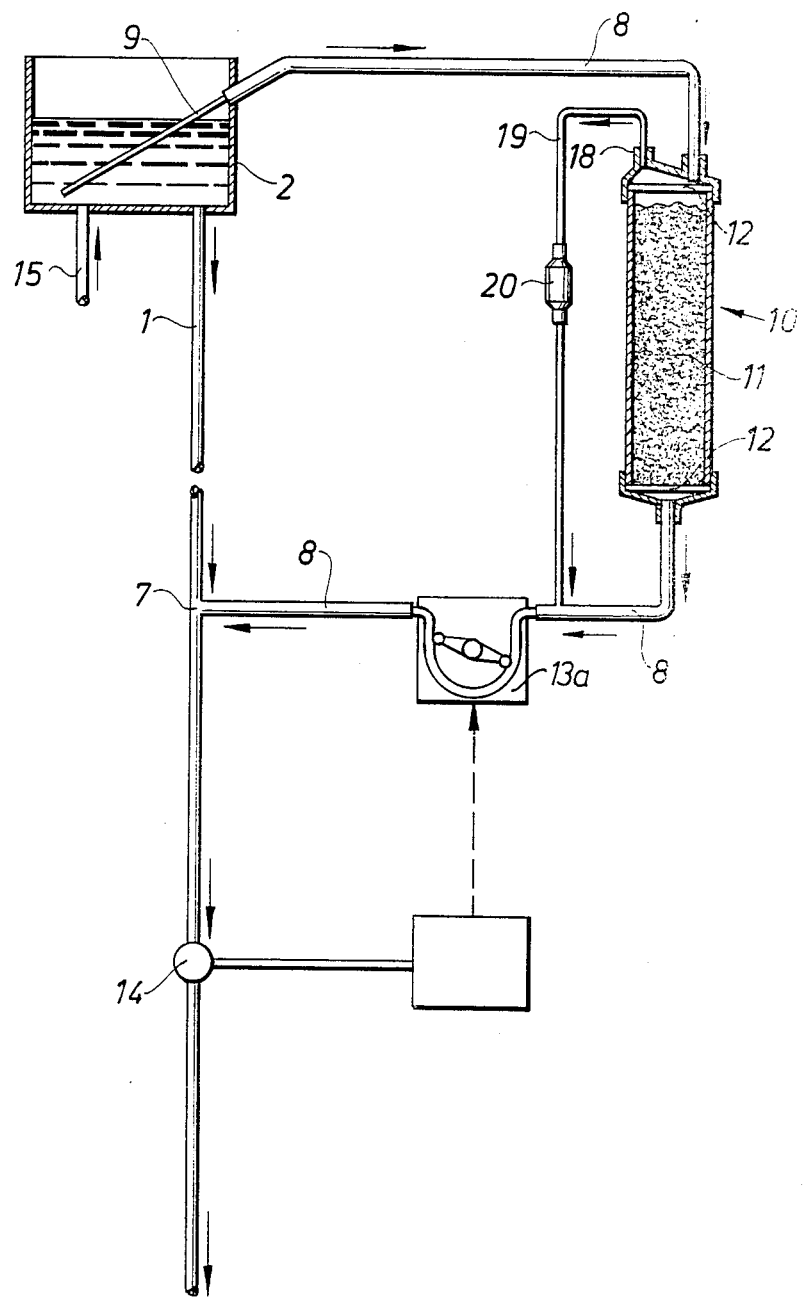

The system shown in FIG. 2 operates in principle in the same manner as that according to FIG. 1. Thus, the same reference numerals have been utilized for corresponding components as were used with respect to the embodiment shown in FIG. 1. To the extent that any of the components have been modified, such components have been indicated through the use of the letter "a" after the referenc numeral.

The system shown in FIG. 2 differs from that according to FIG. 1 mainly through the employment of a mixing pump 13a as the flow regulating device, in place of the throttle device 13 employed in the embodiment of FIG. 1. In this connection, it has been found appropriate to also provide a special deaeration arrangement for the powder concentrate column 10. To this end, a vent opening 18 is provided which is preferably arranged at or near the top of the powder concentrate column or vessel 10. A suction line or duct 19 is connected at one end to the vent 18 and at the other end to the concentrate conduit 8 at a point upstream of the suction pump 13a. The suction line 19 also includes a hydrophobic filter 20 therein. In this manner, suction pressure is produced appropriately in the suction line 19 through the aid of the pump 13a which thus facilitates deaeration of the system, especially during start-up. When the column 10 has been totally deaserated, by liquid drawn into the line 19 will be blocked or stopped upon reaching the hydrophobic filter 20 and, thus, liquid will only be withdrawn from the column 10 via the concentrate conduit 8. Should any new air or other gas be formed in the column 10 during operation, this normally would remain in the uppermost part of the column 10 and, therefore, will not disturb any subsequent measurement. Of course, the system according to FIG. 2 may also include means (not shown) for the deaeration of the main stream being conducted through the primary or main line 1.

Figure 3:
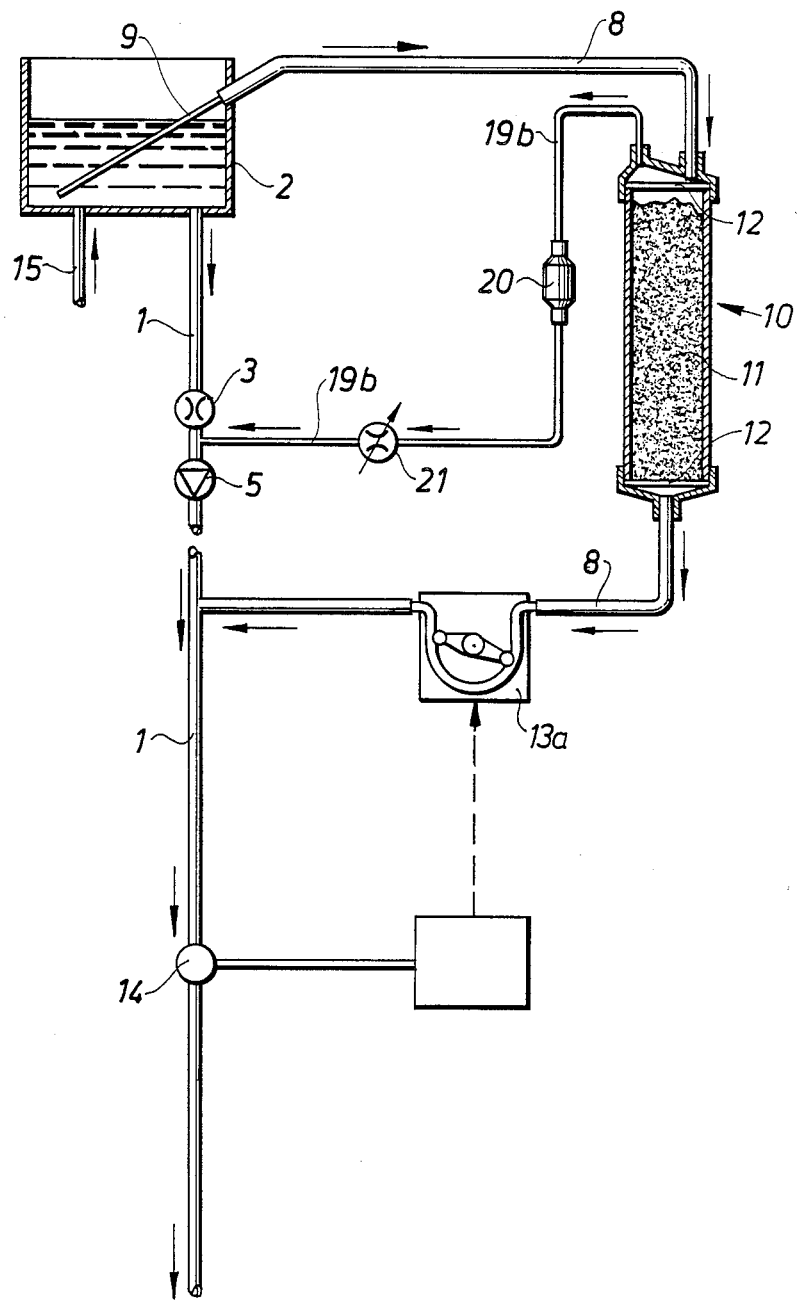

The system according to FIG. 3 also corresponds in principle to that illustrated in FIGS. 1 and 2 and, therefore, the same reference numerals have been used with respect to the same components. Modified components have been indicated through the use of the additional letter "b". The system of FIG. 3 differs from that of FIG. 2 in that the deaeration or suction line 19 has been replaced with a deaeration line 19b which includes a hydrophobic filter 20 arranged therein together with an adjustable throttle device 21. Also, in contrast to the deaeration line 19 shown in FIG. 2, the line 19b does not open directly into the concentrate conduit 8, but rather, communicates with the main line 1 immediately upstream of the pump 5 and downstream of the throttle device 3. In order that the hydrophobic filter 20 not be subjected to the entire negative deaeration pressure during normal operation, the throttle device 21 preferably is adapted so that it is capable of being closed completely when deaeration of the column 10 has been completed.

Figure 4:
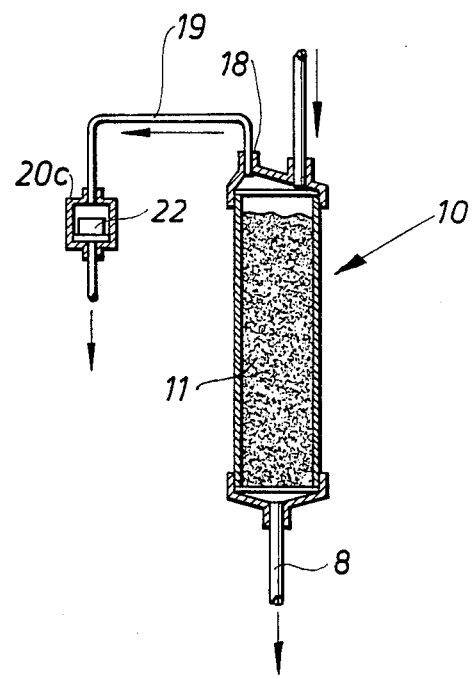

FIG. 4 shows a further alternative arrangement for the concentrate powder column 10 and suction duct 19. In this arrangement, the hydrophobic filter 20 has been replaced by or alternatively used in combination with, an expansible body or material 22 provided within the housing therefor, designated by the reference character 20c, which is adapted to expand upon water being drawn into the housing 20c to thus close off further flow therethrough. Thus, with this arrangement, the line 19 is effectively closed after complete deaeration by means of the expansion of the body 22.

Thus, it will be appreciated that in accordance with the embodiments of the system shown in FIGS. 2, 3 and 4, a separate venting arrangement is provided in the column 10. More particularly, the column 10 is provided with a separate vent opening 18 which preferably is arranged at or near the highest point of the column 10. Deaeration of the system is further facilitated through the aid of a suction line 19 originating from the vent opening 18 in the column and preferably provided with a hydrophobic filter or other shut-off device for the fluid. In this manner, any irregular discharge during normal operation of fluid concentrate through the suction line 19 is prevented. Further, the suction duct 19 connected to the vent opening 18 in the column 10 can communicate either with the concentrate conduit 8 or directly with the main line 1. In each instance, such communication should take place appropriately just upstream of the suction pump 13a or 5 installed in the respective conduit 8 or 1.

Further, in accordance with the preferred embodiments of the present invention, it is to be noted that water is introduced into the concentrate powder column 10 at the top of the column 10 and conducted downwardly to the bottom thereof. This is preferable in order to maintain and provide a relatively constant concentration level of dissolved powder concentrate into the primary fluid line 1. However, it should also be appreciated that water withdrawn into the concentrate fluid line 8 could be conducted through the powder column 10 from the bottom toward the top, both in connection with normal operation as well as in connection with initial priming of the system.

Still further, it should be appreciated that the primary fluid line 1 and concentrate fluid line 8 could both be connected directly to a source of water such as a tap water system, for example, by means of a T-coupling, instead of to a reservoir which is supplied with water. Furthermore, it should also be appreciated that the primary fluid line 1 and concentrate fluid line 8 could be connected to different sources of water, although it is preferable that they both be connected to a common source of water such as reservoir 2 as shown in FIGS. 1-4.

Figure 5:
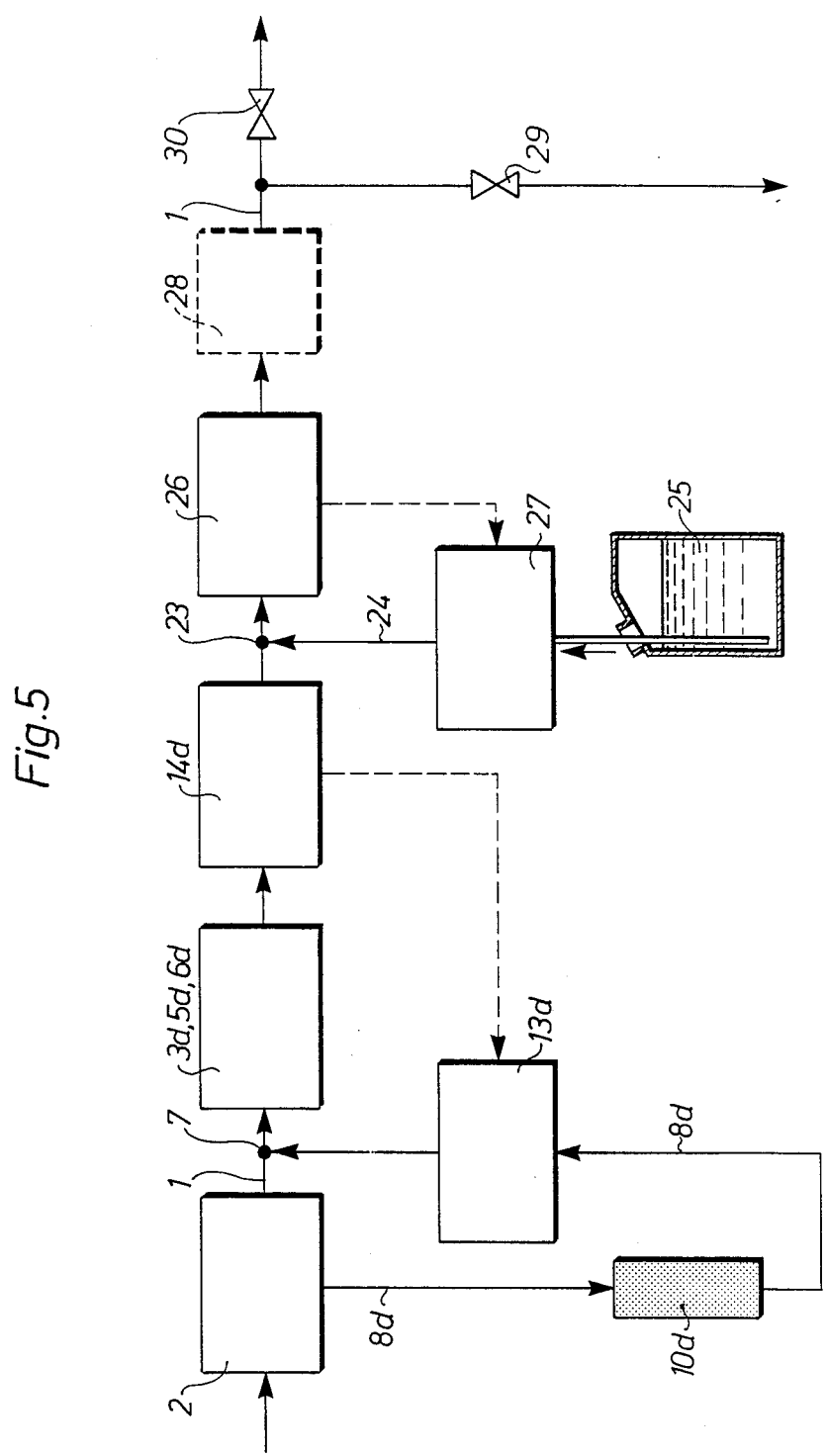
FIG. 5 illustrates a further alternative arrangement for the system of the present invention in which the fluid is prepared starting with one concentrate in powder form and a second concentrate in liquid form.

In certain instances, the solution for a medical procedure or treatment is to be prepared from more than one concentrate, such as, for example, the dialysis solution disclosed in the aforementioned European patent specification EP-B1-0 022 922. In such situations, in accordance with the present invention, the more stable concentrate may be provided in a liquid form and the less stable concentrate or concentrates provided in powder form. In this regard, FIG. 5 illustrates a modified system in accordance with the present invention for preparing a solution for a medical procedure or treatment in which the solution is prepared from one concentrate in powder form and one concentrate in liquid form. Again, in FIG. 5, the same reference characters have been used as in the remaining figures., but with the added letter "d" being used to designate modified components.

In accordance with the modified system shown in FIG. 5, a suitable reservoir 2 is provided from which fluid for preparing a solution is conducted, on the one hand, via a main or primary conduit 1 and, on the other hand, through a concentrate circuit or conduit 8d containing a powder concentrate column 10d therein. The concentrate conduit 8d communicates with the main conduit 1 at a mixing point 7. Means for regulating the flow of fluid in the main conduit 1 and for deaeration, respectively, have been indicated by a single rectangle marked 3d, 5d, 6d. A conductivity meter or other measuring device is provided in the main control 1, as indicated by the reference numeral 14d. The conductivity meter or other measuring device 14d is adapted to control a flow regulating device 13d provided in the concentrate conduit 8d downstream of the powder concentrate column 10d. If the flow regulating device comprises a throttle, such as throttle 13 shown in FIG. 1, the throttle device 3d should be located upstream of the mixing point 7. It will thus be appreciated that the foregoing description of the system according to FIG. 5 substantially corresponds with the systems described hereinabove with reference to FIGS. 1-4. In the system of FIG. 5, however, a second mixing point 23 is provided downstream of the conductivity meter 14d. At mixing point 23, a second concentrate fluid is introduced into the main duct via a second concentrate conduit or duct 24 which communicates with a source of second concentrate 25, which, in this instance, is in a liquid form. The flow of concentrate through the second concentrate duct 24 is regulated with the aid of a conductivity meter or other measuring device 26 provided in the main conduit 1 and which controls a flow regulating device 27 provided in the second concentrate duct 24. For ultimate monitoring of the prepared solution, a pH meter 28 may be installed in the main conduit 1. If conductivity, pH, temperature, or any other parameter utilized for controlling the flow of concentrates through their respective conduits 8d, 24 do not agree or correspond with the desired value, the prepared fluid is passed via a bypass valve 29 directly to a discharge (not shown). If, on the other hand, all of the parameters are correct or in accordance with their desired values, the prepared solution is passed via valve 30 to the actual point of treatment, for example, a dialyzer.

Thus, it will be appreciated that if two concentrates are to be conducted to the main duct 1 at two separate mixing points 7, 23 in the main conduit 1 for mixing with the fluid being conducted through the main conduit 1, conductivity meters or other measuring devices 14d, 26 for accurate monitoring of the composition of the prepared solution upstream as well as downstream of the second mixing point 23 may appropriately be arranged in the main duct 1 and, in particular, arranged downstream of the respective mixing point 7 with which the concentrate conduit 8d communicates.

Figure 6:
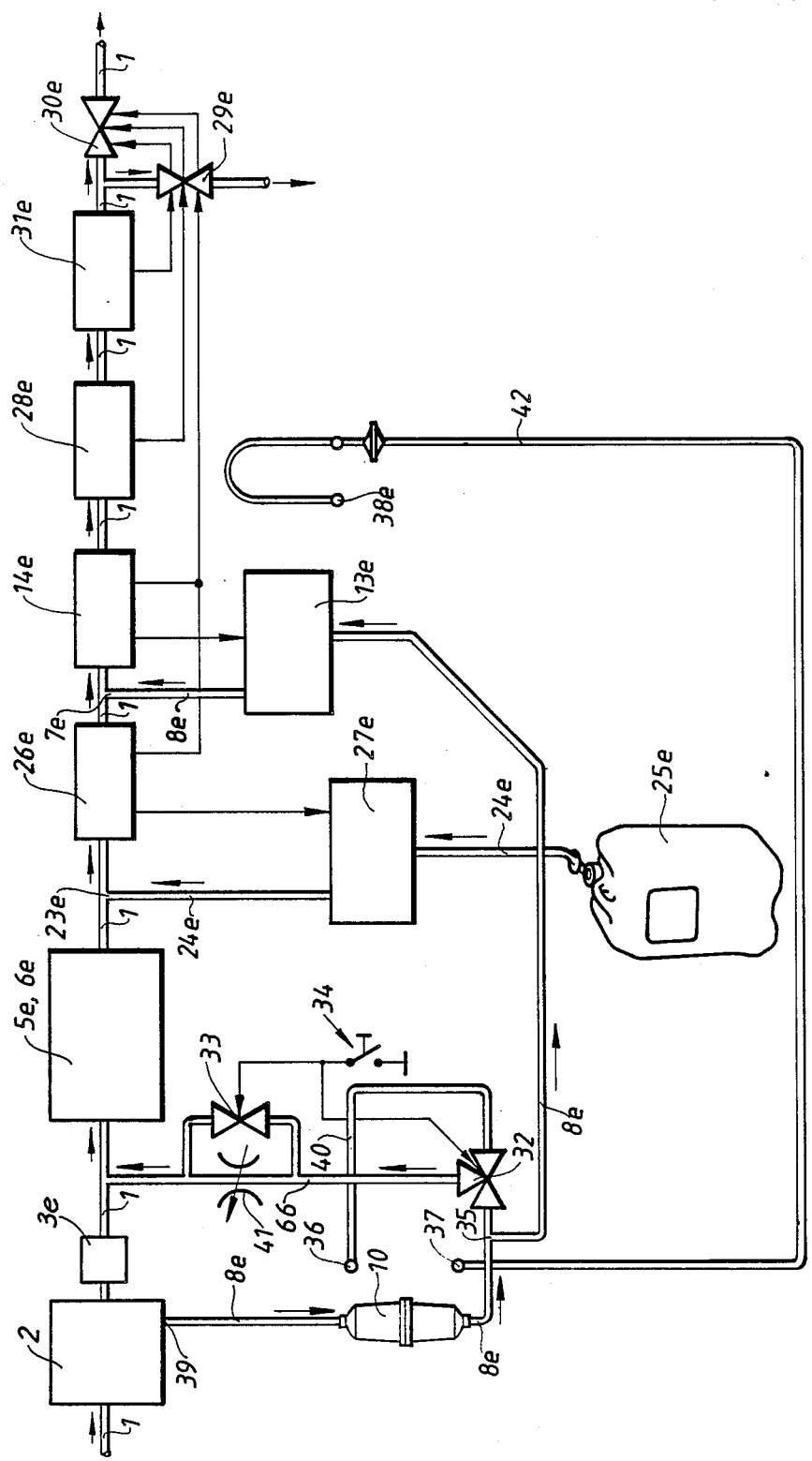
FIG. 6 illustrates a still further arrangement for the system in accordance with the present invention which again utilizes a concentrate in powder form and a concentrate in liquid form, the system of FIG. 6 being particularly adapted for use in connection with a hemodialysis-type of treatment.

FIG. 6 shows a still further modified system in accordance with the principles of the present invention which is particularly intended for use in connection with preparation of a dialysis fluid for use in connection with a hemodialysis operation. Once again, the same reference characters have been used to designate like components, with the added character "e" being included with respect to modified components. The system shown in FIG. 6 is similar to that in accordance with FIG. 5 in that it is used to prepare a solution from two different concentrates, one in liquid form and one in powder form. The system of FIG. 6 differs from FIG. 5, however, with respect to the location the concentrate fluids obtained from the liquid and powder sources are introduced into the main duct or conduit 1.

In accordance with the system of FIG. 6, water for use in preparing the dialysis fluid is introduced to a heating vessel or reservoir 2 for heating the water to the desired temperature. From the heating vessel or reservoir 2, the main part of the water used in preparing the dialysis fluid is conducted from the reservoir 2 through a main or primary conduit 1. In the main conduit 1, the flow is degased by means of a throttle 3e, and a pump 5e and a deaerator 6e, shown together in FIG. 6 as a single rectangle. A liquid concentrate line or duct 24e communicates with the main conduit 1 at a mixing point 23e downstream of the throttle 3e and the rectangle 5e, 6e. The concentrate duct 24e includes a concentrate pump 27e therein which pumps a liquid concentrate from a liquid concentrate container 25e. The conductivity of the mixture after introduction of the liquid concentrate is measured in the main conduit 1 by means of a conductivity meter 26e which controls the pump 27e.

A smaller portion of the water in the reservoir 2 is fed through a concentrate fluid circuit comprised of a concentrate conduit 8e. A column or vessel 10 containing a concentrate in powder form is provided in the concentrate conduit 8e so that, as with the other embodiments discussed hereinabove, the smaller portion of water withdrawn from the reservoir 2 is fed through the column 10 from the top toward the bottom therof, and from there through a continuation of the concentrate conduit 8e to a concentrate pump 13e. From the pump 13e, the concentrate fluid obtained from the vessel 10 is then conducted to the main conduit 1 at a mixing point 7e where it is mixed with the main flow of water from the reservoir 2, which includes the liquid concentrate therein. The conductivity is thereafter measured once again, utilizing the conductivity meter 14e which controls the pump 13e in the concentrate conduit 8e.

For the ultimate monitoring of the prepared solution, a pH meter 28e and a third conductivity meter 31e are arranged in the main conduit 1 downstream of the second mixing point 7e, but upstream of a bypass valve 29e and a main valve 30e through which the system may be connected to a dialyzer. If the measurements obtained in the main conduit 1 from the conductivity meters 26e, 14e, 31e and/or the pH meter 28e are not in accord with the desired values, the main valve 30e is closed and valve 29e opened. For this purpose, the conductivity meters 26e, 14e, 31e and pH meters 28e are all shown as controlling valves 29e and 30e. Although the various meters for measuring the properties of the fluid being conducted through main conduit 1 perferably control the valves 29e and 30e, it will also be appreciated that it is possible instead to control one or more of the pumps 5e, 13e and 27e to stop the conduction of fluid through the various conduits.

The system shown in FIG. 6 also includes means for initial priming of the system and, in particular, the powder concentrate column, as well as means for disinfection or sterilization of the system. More particularly, downstream of the powder concentrate column 10, there is provided a bypass or priming line 66 connected to the concentrate conduit 8e and the main conduit 1 downstream of the throttle 3e and upstream of the pump/deaerator rectangle 5e, 6e. A valve 32 is provided at the point that the priming line 66 is connected to the concentrate conduit 8e. When the system, especially the dry column 10, is to be initially primed with water from the heating vessel or reservoir 2, the valve 32 is opend together with a second valve 33, both controlled by a pressure switch or button 34. The two valves 32, 33 are kept upon until water reaches the point 35 where the bypass line joins the concentrate conduit 8e. Thereafter, the two valves 32, 33 are closed and the water, which is now a concentrate fluid containing dissolved powder concentrate therein, may continue through the concentrate conduit 8e to the pump 13e. An adjustable throttling device 41 may also be provided in the priming line 66 in parallel to the valve 33. This arrangement thus facilitates initial dearation of the system by virtue of air being drawn from the vessel and introduced into the mainline 1 upstream of the deaerator 6e.

For disinfection or sterilization of the system, the powder concentrate vessel or column 10 is removed from the concentrate fluid circuit 8e, and the ends of the concentration conduit 8e normally connected to the vessel 10 are instead connected to connection points 36 adn 37, respectively, of separate sterilization conduits or lines 40 and 42. The liquid concentrate container 25e is also removed, and the concentrate duct 24e connected to a connection point 38e in fluid communication with the sterilization line 42. Furthermore, the start point 39 of the concentrate conduit 8e, normally connected to the heating vessel or reservoir 2, is instead connected to a source of disinfection liquid (not shown). In this manner, disinfection liquid is fed through the starting branch of the concentrate conduit 8e to the connection point 36 where it is conducted through the sterilization line 40 to the valve 32. From valve 32, the disinfection liquid is conducted either through the valve 33 or through the parallel valve 41, in the nature of an adjustable throttling device, to the main conduit 1. From the main conduit 1, the disinfection liquid then passes through the throttle device 3e, pump 5e and dearearato 6e until it reaches the mixing point 23e. At mixing point 23e, one part of the disinfection liquid is conducted through the concentrate line 24e via pump 27e, which has now been reversed. The concentrate line 24e, now connectd to connection point 38e in the sterilization conduit 42, serves to conduct the disinfection liquid through line 42 to the point 37 which is attached to the lower part of the concentrate conduit 8e. From there, the disinfection liquid continues through the concentration conduit 8e via pump 13e and back to the main conduit 1, where it meets the rest of the flow of disinfection liquid being conducted through the main conduit 1 from the mixing point 23e. The disinfection liquid then continues through the main conduit 1 to the end valve 30e.

It will thus be appreciated that the various conduits, deaeration or de-gasing devices, pumps and meters of the system, which are all reusable, can easily be disinfected or sterilized for subsequent treatment operations. This is accomplished simply by removing the sources of concentrate, which are generally designed so as to contain a quantity of concentrate suitable for one treatment operation alone, and connecting the concentrate conduits or lines 8e, 24e normally connected to the concentrate sources 10, 25e to additional disinfectant lines 40, 42 and to a source of disinfection or sterilizing fluid. The additional disinfectant conduits 40, 42 are suitably arranged and connected to the remaining components of the system to insure that disinfection solution is conducted throughout all of the reusable components, namely, the conduit lines 1, 8e, 24e, the various meters 14e, 26e, 28e, 31e, and de-gasing and deaeration devices and pumps 3e, 5e, 6e, 13e, 27e.

Figure 7:
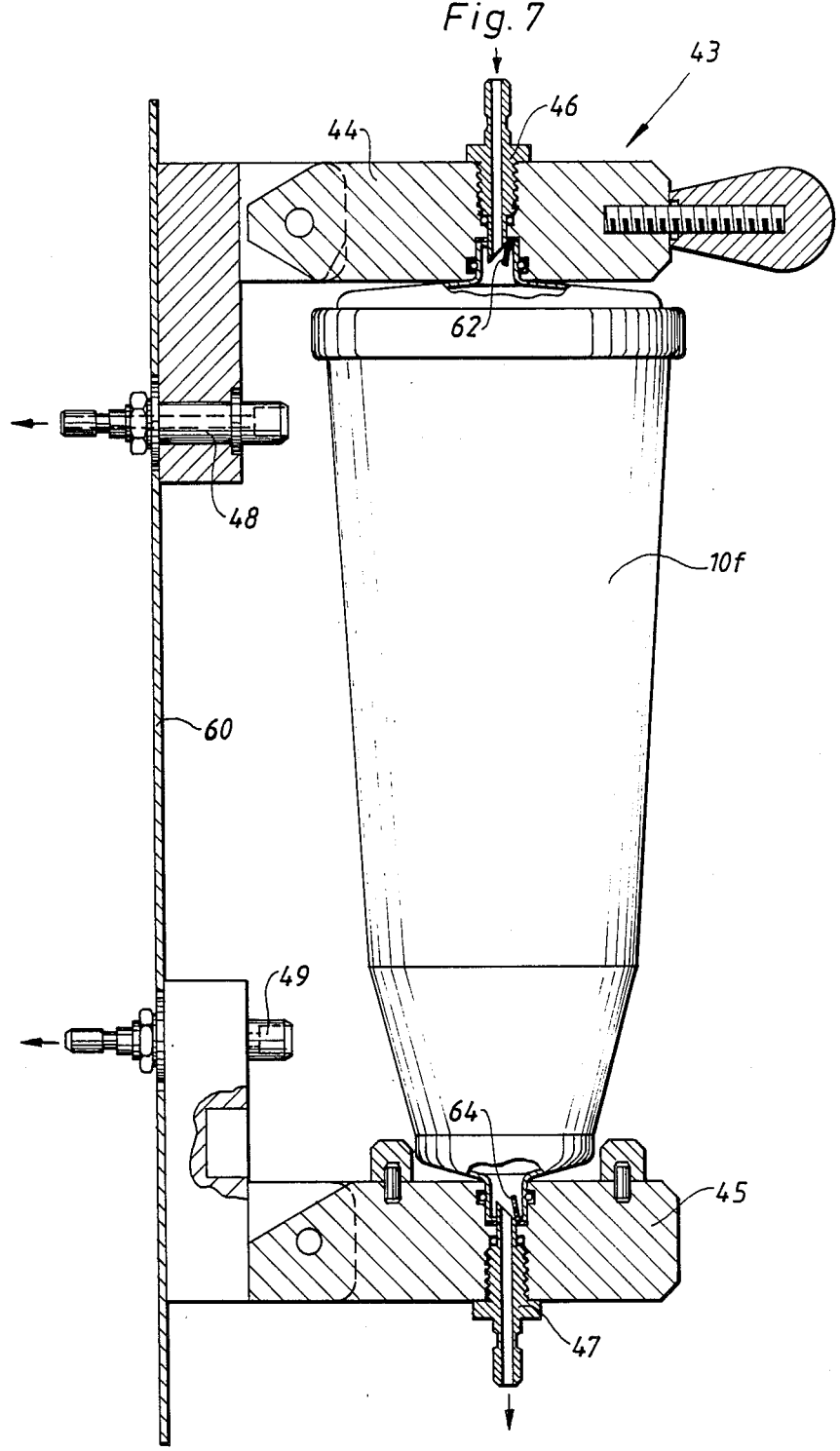
FIG. 7 illustrates a cartridge intended to be used in any of the alternative system arrangements shown in FIGS. 1-6, the cartridge being shown mounted in a holder therefor.

Further in accordance with the present invention, the powder concentrate columns or vessels 10 utilized in the various embodiments described hereinabove may conveniently be in the form of a self-contained cartridge containing a quantity of powder concentrate therein suitable for use one treatment procedure, the cartridge being totally closed and provided with penetrable membranes at its upper inlet and its lower outlets which are adapted to be penetrated by suitable connection devices for the ends of the conduit in the fluid concentrate circuit 8 or 8d or 8e. Also, preferably, the cartridge is internally sterile, such as by having been exposed to radiation such as gamma radiation. FIG. 7 shows such a cartridge 10f, as well as a holder 43 therefor, which is specially constructed to accommodate a cartridge of a particular configuration.

As shown in FIG. 7, the cartridge column 10f comprises a closed vessel provided with penetrable membranes 62, 64 at its upper inlet end and its lower outlet end, respectively. Within the cartridge vessel, there is provided a supply of powder concentrate of sufficient quantity so as to be suitable for a single treatment. For instance, in connection with preparation of a dialysis fluid or solution, the concentrate in powder form may consist of sodium bicarbonate material, and the quantity thereof contained in the cartridge would be on the order of magnitude of 400–900 grams and, more preferably, approximately 600 grams. Also, the contents of the cartridge 10f are preferably sterilized, such as by means of gamma radiation.

Further, in order to obtain an even flow of fluid throught the powder concentrate vessel or column 10f and, thus, a uniform solution of the powder in the fluid, it has been found that there is a preferable minimum particle size for the powder concentrate. For many materials, and especially bicarbonate materials, it has been found that the particles of powder should be of a size of at least 100 microns ($\mu$), and preferably larger than 150 microns ($\mu$). A minor blending in of smaller particles may, however, be acceptable. In this regard, a suitable mixture, for example, may be comprised of powder particles having a size of between 130 and 500 microns ($\mu$).

The cartridge 10f is adapted to be mounted in a holder 43 provided with a pair of upper and lower swinging arms 44 and 45 mounted on a suitable support structure 60. The arms 44, 45 are provided with spike connectors 46 and 47, respectively, which are intended to penetrate the membranes 62, 64 at the upper inlet and the lower outlet of the closed cartridge vessel 10f. In this regard, the upper inlet and lower outlet of the cartridge 10f are each provided with an outwardly portruding nipple having the penetrable membranes 62, 64 therein, which nipples are adapted to be received in suitable recesses in the arms 44, 45 so that the end of the spike connectors 46, 47 may penetrate same when the arms 44, 45 are swung into essentially horizontal positions to hold the cartridge 10f. In this regard, the spacing between the arms 44, 45 is such as to corresond to the height of the cartridge 10f. The upper or inlet spike 46 is intended to be connected to the conduit in the concentrate fluid circuit 8e which is upstream of the cartridge 10 as shown in FIG. 6, whereas the outlet spike 47 is intended to be attached to the concentrate conduit which is downstream of the cartridge 10 in the fluid concentrate circuit 8e. It will thus be appreciated that connection of the cartridge 10f in the circuit 8e is accomplished relatively easily by moving the arms 44, 45 apart, positioning the cartridge 10f therebetween and then moving the arms 44, 45 into horizontal, parallel, positions so that the spikes 46, 47 penetrate the membranes 62, 64.

When the system in accordance with the present invention is to be sterilized or disinfected, it will be appreciated with reference to FIG. 7 that it is a relatively simple operation to remove the cartridge 10f and to connect the spike 46 to a nipple 48 and the spike 47 to a nipple 49 mounted on the support structure 60 for the cartridge 10f. The nipples 48 and 49 correspond to the connection points 36 and 37, respectively, which are schematically shown in FIG. 6.

When an accurate regulation of a plurality of substances which are to be included in a prepared solution for a medicl treatment is desired, two ore more columns or other vessels 10 of powder concentrates of different types may be arranged in the concentrate fluid circuit 8, for example, one column for each of the principal substances to be included in or mixed with the water for preparation of the prepared solution. In this instance, each of the columns 10 for the respective powder concentrates may be of a distinct configuration, such as, distinct with regard to shape, the manner of connection or some other like manner, so that each column or other vessel 10 of powder concentrate which is to be connected to the system may only be connected at the correct point or location within the system. Conveniently, this may be accomplished through the use of different size cartridges 10f and different holders 43 of the type shown in FIG. 7 in which the spacing between the arms 44, 45 is different for the respective, different size cartridge 10f containing powder concentrates.

Figure 8:
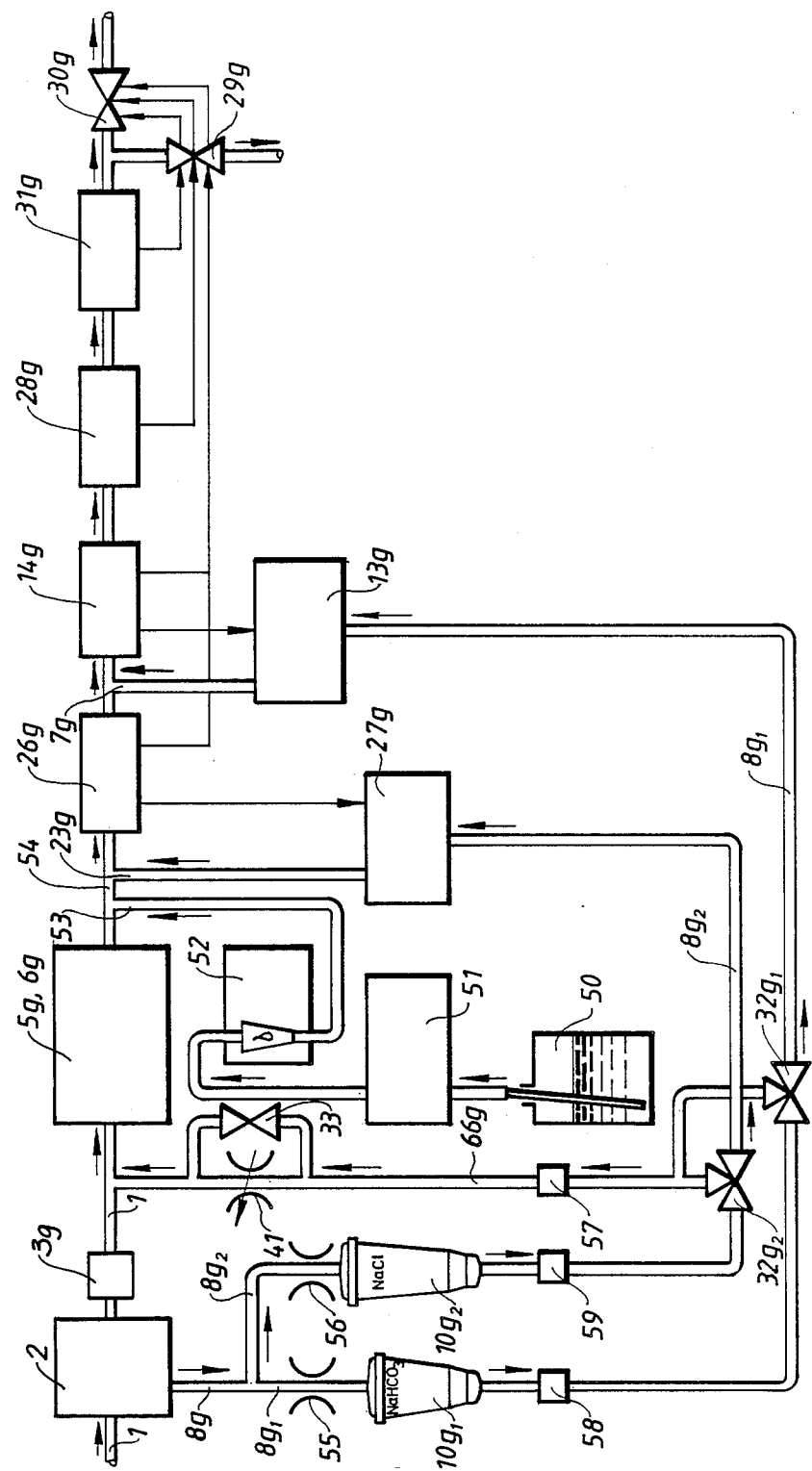
FIG. 8 illustrates a still further arrangement for the system in accordance with the present invention in which two different concentrates in powder form are utilized in connection with a further concentrate in liquid form for preparing a fluid for a medical procedure.

For instance, FIG. 8 schematically shows a still further arrangement for a system in accordance with the present invention in which two different substances in the form of powder concentrates, as well as a liquid concentrate, are used in preparing a solution for a medical treatment. Again, the same reference characters are used in FIG. 8, but with the addition of the character "g" thereafter to indicate modified components. More specifically, the system of FIG. 8 is particularly useful in connection with preparing a dialysis fluid for a dialysis operation which includes two columns or vessels of powder material, one including a bicarbonater material and one including a salt solution, such as sodium chloride, as well as a liquid concentrate such as acid.

As can best be seen in FIG. 8, the two columns $10g_1$ and $10g_2$ containing powder concentrate are in the form of self-contained cartridges similar to that shown in FIG. 7, except that they are of different sizes. Specifically, cartridge $10g_1$ has a shorter height than cartridge $10g_2$. The cartridges $10g_1$ and $10g_2$ are arranged in parallel to one another in the concentrate fluid circuit $8g$ so that each will receive a portion of the water directed from the heating vessel or reservoir 2. The water withdrawn from the reservoir 2 through the concentrate fluid circuit $8g$ flows through the respective cartridges $10g_1$ and $10g_2$ to thus produce two concentrate fluid, each comprised of powder concentrate dissolved in water.

Water is also withdrawn from the heating vessel or reservoir 2 through a main line 1. The concentrate fluids obtained from the two vessels $10g_1$ and $10g_2$ are returned to the main line 1 at two different mixing points, $23g$ and $7g$, respectively, with the mixing points $23g$, $7g$ being separated from one another and with a conductivity meter $26g$ provided therebetween. Liquid concentrate, such as an acid, may be taken from a suitable container or bag 50 by means of a pump 51 which may be controlled in such a manner that a desired value is obtained in a drip counter 52. The concentrate from the drip counter 52 is conducted to the main line or conduit 1 at mixing point 53 which is upstream of the first mixing point $23g$. At a point 54 intermediate the mixing points 53 and $23g$, a further conductivity meter or pH-meter (not shown) may be provided. However, such a meter is not necessary if the pump 51 for the acid is controlled precisely.

The remainder of the system shown in FIG. 8 corresponds essentially to the system according to FIG. 6, with the exception of the modifications for accommodating two different size powder concentrate cartridges $10g_1$ and $10g_2$. As shown in FIG. 8, the concentrate fluid circuit $8g$ includes two parallel branch lines $8g_1$ and $8g_2$, with one cartridge $10g_1$ being arranged in one branch line $8g_1$, and the other cartridge $10g_2$ arranged in the other branch line $8g_2$. Conveniently, a holder such as holder 43 shown in FIG. 7 but sized to accommodate cartridge $10g_1$ can be used to hold cartridge $10g_1$ in position in branch line $8g_1$, whereas a larger sized holder can be used to hold cartridge $10g_2$ in branch line $8g_2$. In this way, only cartridge $10g_1$ can be positioned in line $8g_1$ and only cartridge $10g_2$ positioned in line $8g_2$. This thus provides a degree of protection against improperly connecting the cartridges $10g_1$, $10g_2$ to the system. Of course, different connection means, such as different manners of connecting the conduits to the cartridge $10g_1$, $10g_2$, particular shapes for the cartridges and holder therefor, or other special configurations, could be used for insuring that the cartridges can be connected to the system only at the correct locations.

Branch line $8g_1$ includes a pump $13g$ therein downstream of cartridge $10g_1$ for conducting concentrate fluid produced in cartridge $10g_1$ to the main conduit 1 at mixing point $7g$, whereas brand line $8g_2$ includes a pump $27g$ therein downstream of cartridge $10g_2$ for conducting concentrate fluid produced in cartridge $10g_2$ to the main conduit 1 at mixing point $23g$. A separate priming line $66g$ is also provided, connected to each of the branch lines $8g_1$, $8g_2$ via means of vavles $32g_1$, $32g_2$ downstream of the respective cartridges $10g_1$, $10g_2$ and communicating with main line 1 intermediate the throttle device $3g$ and the pump/deaerator rectangle $5g$, $6g$. The priming line $66g$ is for a similar purpose as the priming line 66 shown in FIG. 6.

By way of example, for preparation of a dialysis fluid, the cartridge $10g_1$ may contain a bicarbonate material in powder form, such as sodium bibarbonate, whereas the cartridge $10g_2$ may contain a different concentrate powder form, such as sodium chloride powder. In this instance, the quantity of sodium bicarbonate in cartridge $10g_1$ may be on the order of 400–900 grams and, more preferably, approximately 600 grams, whereas the quantity of sodium chloride in the cartridge $10g_2$ would preferably be on the order of 1,00–3,000 grams and, more preferably, 1,300–2,700 grams and, still more preferably, approximately 1,400 grams. Such cartridges $10g_1$ and $10g_2$ for use in connection with preparation of a dialysis fluid, i.e., a cartridge $10g_1$ containing bicarbonate material and a cartridge $10g_2$ containing sodium chloride material, both in powder form, may also be used in practice, together with a liquid concentrate 50 which contains other substances necessary for the treatment, such as, for example, acid, calcium, potassium, magnesium, glucose, or the like. A suitable composition for the liquid concentrate 50, for example, may be as follows:

| | |
|---|---|
| $CH_3COOH$ | 44.17 g |
| KCl | 36.54 g |
| $CaCl_2 + 6H_2O$ | 93.94 g |
| $MgCl_2 + 6H_2O$ | 24.92 g |
| $H_2O$ | 210 g |
| Total approx. | 410 g |

The quantities provided in the example hereinabove correspond to that necessary for one treatment operation or procedure, with the quantity of water being determined so that no precipitation should be able to occur during storage at refrigerating cabinet temperature. With a smaller quantity of water, there is a risk of precipitation. In the example above, it will be appreciated that instead of acidic acid, other acids could be used, such as, for example, hydrochloric acid or citric acid.

Preferably, in the system shown in FIG. 8, suitable restrictions 55 and 56 are provided in the respective branch concentrate lines $8g_1$ and $8g_2$ prior to or upstream of the respective cartridges $10g_1$ and $10g_2$. These restrictions 55, 56 are useful in obtaining a subpressure in the two cartridges $10g_1$, $10g_2$ during initial priming of the circuit $8g_2$. Priming is thereafter stopped, and additional suction of water into the cartridge $10g_1$, $10g_2$ is insured, thus providing a feature of security that water will cover the powder, even if an air cushion is provided at the top of each cartridge $10g_1$, $10g_2$.

Also, preferably air or water detectors are provided so that one can determine if the cartridges $10g_1$, $10g_2$ have been filled with water. Further, the detectors may be used for checking that the cartridges $10g_1$, $10g_2$ did not include any water therein when the system was initially started or primed. Here it should be noted that if a column or cartridge 10 is filled with water and left therein for any period of time, either because the concentrate fluid produced is unused or only partly used, there is a risk that the dry powder, stable in and of itself, may be altered or that bacteria growth may occur within the cartridge or column 10. For this purpose, as shown in FIG. 8, an air or water detector 57 may be provided in the priming line and/or separate detectors 58 and 59 may be arranged directly downstream of the respective cartridges $10g_1$, $10g_2$ for checking whether the cartridge $10g_1$, $10g_2$ contain any water at the start of a treatment operation, i.e., to insure that they have not been partly used previously or, for other reasons, contain liquid therein. Such detectors 57, 58, 59, for example, may be in the form of normally dry electrodes arranged inside the priming and/or branch conduit lines $66g$, $8g_1$, $8g_2$, or could even be arranged inside the cartridges or columns $10g_1$, $10g_2$. Alternatively, conductivity meters could be employed in the system which show a deflection only when air included in the system has passed therethrough. Here it should be noted that if the presence of water is detected in the cartridges or columns, suitable alarms can be actuated for insuring that the prepared solution is not delivered to the dialyzer, such as, for example, by closing of the valve $30g$ and opening of the valve $29g$.

Further with respect to the embodiment of the system shown in FIG. 8, it should be noted that the acid from the container 50 may instead be fed into the concentrate line $8g_2$ upstream of the pump $27g$, thus providing the advantage that the acid is fed to a line which has a more constant pressure. Here is should be noted that the pressure of the fluid within the main line 1 may vary, whereas, the pressure within the lines $8g_1$, $8g_2$ is more constant. Thus, by such a construction, the risk is less that fluid would be conducted into the tank or container 50, or sucked thereoutof without any suitable control.

Still further, as with the systems of the present invention described by way of the other embodiments hereinabove, an alarm may suitably be provided to protect against an incorrect conductivity value being measured by the various conductivity measuring devices $26g$, $14g$ or $31g$ or the values measured by the pH meter $28g$, or by any other meters. Additionally, an alarm could also be generated if there is an absence of any acid from the container 50 present in the drip counter 52. Conveniently, the container 50 for the acid may comprise a plastic bag which can conveniently be connected to the system by means of a suitable coupling device, such as, for example, that described and shown in U.S. Pat. No. 4,636,204. As for the acid pump 51, a volumetric-type pump may be utilized which provides the desired flow of acid through the drip counter 52. Still further, in addition to the arrangement of the acid or liquid concentrate being introduced into the main line 1, the liquid or acid from the container 50 may also be fed to a point in the main line 1 which is downstream of the conductivity meters $14g$ and $26g$, which would provide the advantage that the conductivity meters $14g$, $26g$ would not be influenced by the introduction of acid into the main line 1.

It will thus be apparent from the foregoing description that the present invention provides a system for preparing a fluid intended for a medical procedure by mixing of at least one concentrate in a powder form. The system in accordance with the present invention comprises a reservoir 2 for a source of water, and at least one vessel 10 for containing a concentrate in powder form, and a fluid conducting circuit 8 for withdrawing a small quantity of water from the reservoir 2 and passing same through the vessel 10 containing the concentrate in powder form in order to dissolve the concentrate before it is mixed with the rest of the wate withdrawn from the reservoir 2 through a main or primary fluid conducting means 1 downstream of the liquid-containing reservoir 2. In accordance with one aspect of the present invention, measuring means 14 are provided in the primary fluid conduit means 1 downstream of the mixing point 7 for measuring the composition of the prepared solution obtained by mixing of the produced concentrate fluid in the concentrate fluid circuit 8 with water being conducted through the primary circuit 1, and flow regulating means 13 provided in the concentrate fluid circuit 8 downstream of the concentrate vessel 10 which is responsive to the measuring means 13 for controlling the flow of concentrate fluid from the vessel 10.

In accordance with a further aspect of the present invention, a source of second concentrate fluid 25, $10g_2$ is provided as well, and fluid conducting means 24 are provided for introducing the second concentrate fluid into the primary fluid conducting means 1 at a second mixing point 23 therein to be mixed with fluid being conducted therethrough to thereby produce a prepared solution downstream of the two mixing points 7, 23, the prepared solution being comprised of a mixture of water with a first concentrate fluid produced by conducting water from the reservoir 2 into the vessel 10, $10g_1$ containing the concentrate in powder form and a second concentrate fluid from the source 25, $10g_2$ thereof. In one embodiment of the present invention, the source of second concentrate fluid comprises a concentrate in liquid form 25, whereas, in a further embodiment of the present invention, the second concentrate fluid is produced by conducting water from the reservoir 2 through a second vessel $10g_2$ containing powdered concentrate therein to dissolve the second powdered concentrate in the water to produce the second concentrate fluid.

In accordance with a still further aspect of the present invention, the vessel 10 containing the concentrate in powder form therein includes an inlet at the top thereof and an outlet of the bottom thereof, with the vessel 10 being arranged in the concentrate fluid circuit 8 so that water withdrawn from the reservoir 2 is introduced into the top of the vessel 10 to produce a concentrate fluid containing dissolved powder concentrate therein, and so that the concentrate fluid is withdrawn from the bottom of the vessel 10 and conducted to the primary fluid conducting means 1 to be mixed with water being conducted therethrough. In this manner, water is conducted through the powder concentrate vessel 10 from the top thereof to the bottom thereof to thereby maintain and provide a relatively constant concentration level of dissolved powder concentrate. Conveniently, the powder concentrate vessel 10 may comprise a normally completely closed cartridge 10f, having penetrable membranes 62, 64 at its inlet and outlet outlets which are adatped to be penetrated upon being connected to the concentrate fluid circuit 8. The cartridge 10f contains a quantity of powder concentrate therein suitable for one treatment procedure. In this manner, for different treatment operations, it is only necessary to connect new cartridges 10 and/or other sources 25, 50 of liquid concentrate to the system, with the remaining components of the system being reusable for different medical procedures or treatments.

As will be readily apparent to those skilled in the art, the present invention may be used in other specific forms without departing from its spirit or essential characteristics. For example, the components included in the system may be varied within wide limits, both with regard to their form and their function. Furthermore, it will be apparent to those versed in the art that the system of the present invention can readily be modified by combinations of one or more powder concentrates, either alone of in further combination with one or more liquid concentrates, for producing a desired prepared solution for a medical procedure or treatment. The preferred embodiments described hereinabove are therefore to be considered as illustrative and not restrictive, the scope of the invention being indicated by the claims rather than the foregoing description, and all changes which come within the meaning or range of equivalents of the claims are therefor intended to be embraced therein.

What is claimed is:

1. A system for preparing a fluid for a medical procedure by mixing of at least one concentrate in powder form with water, said system comprising:
   a source of water;
   a vessel for containing a concentrate in powder form;
   first fluid conducting means having a first end communicating with said source of water for withdrawing water from said source of water, and a second end for delivering a prepared solution;
   second fluid conducting means communicating with said source or water and with an inlet of said vessel for introducing water from said source of water into said vessel to produce a concentrate fluid containing dissolved powder concentrate in water;
   third fluid conducting means communicating with an outlet of said vessel and with a mixing point in said first fluid conducting means intermediate said first and second ends for conducting said concentrate fluid from said vessel into said first fluid conducting means to be mixed with fluid being conducted through said first fluid conducting means to thereby produce a prepared solution in said first fluid conducting means for delivery to said second end of said first fluid conducting means;
   measuring means in said first fluid conducting means downstream of said mixing point for measuring the composition of the prepared solution obtained by mixing of said concentrate fluid and water in said first fluid conducting means; and
   flow regulating means in said third fluid conducting means responsive to said measuring means for controlling the flow of said concentrate fluid from said vessel.

2. The system of claim 1 wherein said source of water comprises a reservoir for containing water.

3. The system of claim 2 wherein said measuring means comprises a conductivity measuring device.

4. The system of claim 2 wherein said flow regulating means comprises a throttling device.

5. The system of claim 4 further including a suction pump arranged in said first fluid conducting means downstream of said mixing point for conducting water from said reservoir through said first fluid conducting means and for conducting water from said reservoir through said second and third fluid conducting means.

6. The system of claim 5 further including a throttling device arranged in said first fluid conducting means intermediate said reservoir and said mixing point, and further including a deaerating device arranged in said first fluid conducting means downstream of said suction pump.

7. The system of claim 1 wherein said flow regulating means comprises a suction pump.

8. The system of claim 1 wherein said inlet of said vessel is at the top thereof and said outlet of said vessel is at the bottom thereof so that water is conducted through said vessel from the top thereof to the bottom thereof to thereby maintain a relatively constant concentration level of dissolved powder concentrate in said third fluid conducting means.

9. The system of claim 1 wherein said vessel includes a vent opening therein arranged at the top of said vessel.

10. The system of claim 9 further including a fluid line communicating with said vent opening in said vessel and having shut-off means arranged therein operative to prevent the flow of liquid from said vessel through said fluid line.

11. The system of claim 10 wherein said flow regulating means comprises a suction pump arranged in said third fluid conducting means and wherein said fluid line communicates with said third fluid conducting means upstream of said suction pump.

12. The system of claim 10 wherein said first fluid containing means includes a suction pump arranged therein for withdrawing water from said source of water, and wherein said fluid line communicates with said first fluid conducting means upstream of said suction pump.

13. The system of claim 10 wherein said shut-off means comprises a hydrophobic filter arranged in said fluid line.

14. The system of claim 10 wherein said shut-off means comprises a housing arranged in said fluid line and having an expansible body provided therein adapted to expand upon liquid being drawn into said housing to prevent the further flow of fluid through said housing.

15. The system of claim 10 wherein said shut-off means comprises an adjustable throttling device in said fluid line adapted to be closed after deaeration of said vessel.

16. The system of claim 1 wherein said vessel comprises a first vessel containing a fluid concentrate in powder form, and wherein said system further includes a source of second concentrate fluid and means for introducing said second concentrate fluid into said first fluid conducting means to be mixed with said first concentrate fluid and water being conducted through said first fluid conducting means.

17. The system of claim 16 wherein said source of second concentrate fluid comprises a source of second concentrate in liquid form.

18. The system of claim 17 wherein said mixing point comprises a first mixing point, and wherein said means for introducing comprises fourth fluid conducting means communicatig with said source of second concentrate and with a second mixing point in said first fluid conducting means intermediate said first and second ends and spaced from said first mixing point for conducting said second concentrate fluid into said first fluid conducting means.

19. The system of claim 16 wherein said source of second concentrate fluid comprises a second vessel containing a second concentrate in powder form, and fourth fluid conducting means communicating with said source of waer and an inlet of said second vessel for introducing water from said source of water into said second vessel to produce said second concentrate fluid.

20. The system of claim 19 wherein said mixing point comprises a first mixing point; and wherein said means for introducing comprises fifth fluid conducting means communicating with an outlet of said second vessel and with a second mixing point in said first fluid conducting means intermediate said first and second ends and spaced from said first mixing point for conducting said second concentrate fluid into said first fluid conducting means.

21. The system of claim 1 wherein said vessel contains a concentrate in powder form having a particle size which is greater than 100 microns.

22. The system of claim 21 wherein said concentrate in powder form comprises a bicarbonate material having a particle size between 130 and 500 microns.

23. The system of claim 1 further including water determining means for determining if water is present in said vessel.

24. The system of claim 23 further including alarm means for generating an alarm signal if water is present in said vessel prior to start-up of said system, said alarm means being responsive to said water determining means.

25. The system of claim 1 wherein said vessel comprises a self-contained cartridge containing a quantity of concentrate in powder form therein which is suitable for one treatment procedure.

26. The system of claim 25 wherein said cartridge comprises a closed vessel having penetrable membranes at said inlet and said outlet thereof, and wherein said second and third fluid conducting means communicate with said inlet and said outlet respectively of said closed vessel through said penetrable membranes.

27. The system of claim 26 further including connecting devices for controlling said second and third fluid conducting means to said cartridge vessel, said connecting devices each having a first end for penetrating one of said penetrable membranes and a second end to which one of said fluid conducting means is connected.

28. The system of claim 27 further including a holder for holding said vessel and wherein said connecting devices are mounted to said holder.

29. The system of claim 25 wherein the contents of said cartridge are internally sterilized.

30. The system of claim 29 wherein the contents of said cartridge are sterilized by means of radiation.

31. The system of claim 30 wherein the contents of said cartridge are sterilized by means of gamma radiation.

32. The system of claim 25 wherein said cartridge contains a bicarbonate material in powder form, the quantity of said bicarbonate material in said cartridge being on the order of 400 to 900 grams.

33. The system of claim 32 wherein the quantity of bicarbonate material contained in said cartridge is approximately 600 grams.

34. The system of claim 32 wherein said bicarbonate material comprises sodium bircarbonate material.

35. The system of claim 25 wherein said cartridge contains a salt material in powder form, the quantity of salt material contained in said cartridge being on the order of 1,000 to 3000 grams.

36. The system of claim 35 wherein the quantity of salt material contained in said cartridge is on the order of 1,300 to 2,700 grams.

37. The system of claim 36 wherein the quantity of salt material contained in said cartridge is approximately 1,400 grams.

38. The system of claim 35 wherein said salt material comprises sodium chloride material.

39. The system of claim 1 wherein said vessel comprises a first vessel containing a first concentrate in powder form; and wherein said system further includes a second vessel containing a second concentrate in powder form, a source of liquid concentrate, fourth fluid conducting means communicating with said source of water for introducing water into said second vessel to produce a second concentrate fluid containing dissolved second powder concentrate therein and for conducting said second concentrate fluid from said second vessel into said first fluid conducting means intermediate said first and second ends to be mixed with fluid being conducted through said first fluid conducting means, and fifth fluid conducting means communicating with said source of liquid concentrate for withdrawing liquid concentrate from said source of liquid concentrate and introducing said liquid concentrate into said first fluid conducting means intermediate said first and second ends to be mixed with fluid being conducted through said first fluid conducting means, whereby said prepared solution is comprised of said first concentrate fluid, said second concentrate fluid and said liquid concentrate mixed with water withdrawn from said source of water through said first fluid conducting means.

40. The system of claim 39 wherein said first vessel contains a bicarbonate material in powder form, and said second vessel contains a salt material in powder form.

41. The system of claim 40 wherein said liquid concentrate contains a substance selected from the group consisting of an acid, calcium, potassium, magnesium, and glucose.

42. The system of claim 1 wherein said first fluid conducting means includes primary flow regulating means for regulating the flow of fluid through said first fluid conducting means, said primary flow regulating means being operative to provide a flow rate of up to at least 500 ml./min. through said first fluid conducting means downstream of said mixing point.

43. The system of claim 42 wherein said flow regulating means in said third fluid conducting means is operative to provide a flow rate of up to at least 30 ml./min. of concentrate fluid through said third fluid conducting means.

44. The system of claim 43 wherein said primary flow regulating means is operative to provide a flow rate of up to approximately 1,000 ml./min. through said first fluid conducting means downstream of said mixing point and said flow regulating means in said third fluid conducting means is operative to provide a flow rate of up to approximately 40 ml./min. through said third fluid conducting means.

45. The system of claim 1 further including means for priming said system, said means for priming including valve means in said third fluid conducting means intermediate said vessel and said flow regulating means and a priming fluid line connected to said valve means and to said first fluid conducting means intermediate said source of water and said mixing point, said valve means being operative to open said priming line to communicate with said third fluid conducting means for priming of said system and operative to close communication between said priming line and said third fluid conducting means after said system has been primed.

46. The system of claim 1 further including means for disinfection of said system, said means for disinfection including a source of disinfecting solution and disinfecting fluid lines for interconnecting said first, second and third fluid conducting means in a manner to conduct disinfecting solution from said source of disinfecting solution through said fluid conducting means, said measuring means and said flow regulating means.

47. A system for preparing a fluid for a medical procedure by mixing of at least one concentrate in powder form with water, said system comprising:
  a source of water;
  a vessel for containing a concentrate in powder form;
  first fluid conducting means having a first end communicating with said source of water for withdrawing water from said source of water, and a second end for delivering a prepared fluid;
  second fluid conducting means communicating with said source of water and with an inlet of said vessel for introducing water withdrawn from said source of water into said vessel to produce a first concentrate fluid containing dissolved powder concentrate in water;
  third fluid conducting means communicating with an outlet of said vessel and with a first mixing point in said first fluid conducting means intermediate said first and second ends for conducting said first concentrate fluid from said vessel into said first fluid conducting means to be mixed with fluid being conducted through said first fluid conducting means;
  a source of second concentrate fluid;
  fourth fluid conducting means having a first end communicating with said source of second concentrate fluid and a second end communicating with said first fluid conducting means at a second mixing point intermediate said first and second ends of said first fluid conducting means for introducing into said first fluid conducting means said second concentrate fluid to be mixed with fluid being conducted through said first fluid conducting means, to thereby produce a prepared solution in said first fluid conducting means downstream of said first and second mixing points for delivery to said second end of said first fluid conducting means, said prepared solution being comprised of said first concentrate fluid and said second concentrate fluid mixed with water withdrawn from said source of water through said first fluid conducting means.

48. The system of claim 47 further including first and second measuring means in said first fluid conducting means, said first measuring means being downstream of said first mixing point and operative to measure the composition of fluid in said first fluid conducting means downstream of said first mixing point and said second measuring means being downstream of said second mixing point and operative to measure the composition of fluid in said first fluid conducting means downstream of said second mixing point.

49. The system of claim 48 further including first flow regulating means responsive to said first measuring means for controlling the flow of said first concentrate fluid through said third fluid conducting means, and second flow regulating means responsive to said second measuring means for controlling the flow of said second concentrate fluid through said fourth fluid conducting means.

50. The system of claim 49 wherein said first and second flow regulating means each comprise a suction pump.

51. The system of claim 49 further including a throttling device, a suction pump and a dearating device arranged in said first fluid conducting means.

52. The system of claim 51 wherein said throttling device, said suction pump and said dearating device are all arranged in said first fluid conducting means downstream of said source of water and upstream of both of said first and second mixing points.

53. The system of claim 48 wherein said first and second measuring means each comprise a conductivity measuring device.

54. The system of claim 47 wherein said inlet of said vessel is at the top thereof and said outlet of said vessel is at the bottom thereof so that water is conducted through said vessel from the top thereof to the bottom thereof to thereby maintain a relatively constant concentration level of dissolved powder concentration in said third fluid conducting means.

55. The system of claim 47 wherein said source of second concentrate fluid comprises a source of second concentrate in liquid form.

56. The system of claim 47 wherein said vessel contains a concentrate in powder form having a particle size which is greater than 100 microns.

57. The system of claim 47 further including water determining means for determining if water is present in said vessel.

58. The system of claim 57 further including alarm means for generating an alarm signal if water is present in said vessel prior to start-up of said system, said alarm means being responsive to said water determining means.

59. The system of claim 47 wherein said vessel comprises a self-contained cartridge containing a quantity of concentrate in powder form therein which is suitable for one treatment procedure.

60. The system of claim 59 wherein said cartridge comprises a closed vessel having penetrable membranes at said inlet and said outlet thereof, and wherein said second and third fluid conducting means communicate with said inlet and said outlet respectively of said closed vessel through said penetrable membranes.

61. The system of claim 60 further including connecting devices for connecting said second and third fluid containing means to said cartridge vessel, said connecting devices each having a first end for penetrating one of said penetrable membranes and a second end to which one of said fluid conducting means is connected.

62. The system of claim 61 further including a holder for holding said vessel and wherein said connecting devices are mounted to said holder.

63. The system of claim 59 wherein the contents of said cartridge are internally sterilized.

64. The system of claim 59 wherein said cartridge contains a bicarbonate material in powder form, the quantity of said bicarbonate material in said cartridge being on the order of 400 to 900 grams.

65. The system of claim 59 wherein said cartridge contains a salt material in powder form, the quantity of salt material contained in said cartridge being on the order of 1,000 to 3,000 grams.

66. The system of claim 47 wherein said source of water comprises a reservoir for containing water.

67. The system of claim 66 wherein said source of second concentrate fluid comprises a second vessel containing a second concentrate in powder form and fifth fluid conducting means communicating with said reservoir and an inlet of said secod vessel for introducing water from said reservoir into said second vessel to produce said second concentrate fluid.

68. The system of claim 66 wherein said vessel comprises a first vessel containing a first concentrate in powder form and said source of second fluid concentrate comprises a source of liquid concentrate; and wherein said system further includes a second vessel containing a second concentrate in powder form, fifth fluid conducting means communicating with said reservoir for introducing water from said reservoir into said second vessel to produce a third concentrate fluid containing dissolved second powder concentrate therein and for conducting said third concentrate fluid from said second vessel into said first fluid conducting means intermediate said first and second mixing points to be mixed with fluid being conducted through said first fluid conducting means, whereby said prepared solution is comprised of said first concentrate fluid, said second concentrate fluid and said third concentrate fluid mixed with water withdrawn from said reservoir through said first fluid conducting means.

69. The system of claim 68 wherein said first vessel contains a bicarbonate material in powder form and said second vessel contains a salt material in powder form.

70. The system of claim 69 wherein said second concentrate fluid contains a substance selected from the group consisting of an acid, calcium, potassium, magnesium, and glucose.

71. The system of claim 66 further including means for priming said system, said means for priming including valve means in said third fluid conducting means intermediate said vessel and said flow regulating means and a priming fluid line connected to said valve means and to said first fluid conducting means intermediate said reservoir and said mixing point, said valve means being operative to open said priming line to communicate with said third fluid conducting means for priming of said system and operative to close communication between said priming line and said third fluid conducting means after said system has been primed.

72. The system of claim 66 further including means for disinfection of said system, said means for disinfection including a source of disinfecting solution and disinfecting fluid lines for interconnecting means in a manner to conduct disinfecting solution from said source of disinfecting solution through said fluid conducting means, said measuring means and said flow regulating means.

73. A system for preparing a fluid for a medical procedure by mixing of at least two concentrates in powder form with water, said system comprising:

a source of water;
a first vessel for containing a first concentrate in powder form;
a second vessel for containing a second concentrate in powder form, said second concentrate being different from said first concentrate;
first fluid conducting means having a first end communicating with said source of water for withdrawing water from said source of water, and a second end for delivering a prepared solution;
a concentrate fluid circuit communicating with said source of water and with said first fluid conducting means intermediate said first and second ends of said first fluid conducting means for conducting fluid containing water from said source of water through said concentrate fluid circuit and into said first fluid conducting means upstream of said second end of said first fluid conducting means to be mixed with fluid being conducted throough said first fluid conducting means to thereby produce a prepared solution for delivery to said second end of said first fluid conducting means, said prepared solution being comprised of fluid from said concentrate fluid circuit mixed with water withdrawn from said source of water; and
said concentrate fluid circuit including first connection means at a first location in said concentrate fluid circuit for connecting said first vessel to said concentrate fluid circuit so as to introduce fluid containing water from said source of water into said first vessel to dissolve said first concentrate and to withdraw fluid containing said dissolved first concentrate from said first vessel, and second connection means at a second location in said concentrate fluid circuit for connecting said second vessel to said concentrate fluid circuit so as to introduce fluid containing water from said source of water into said second vessel to dissolve said second concentrate and to withdraw fluid containing said dissolved second concentrate from said second vessel, said first and second connection means being different from one another so that said first vessel is only connectable to said concentrate fluid circuit at said first location by said first connection means and said second vessel is only connectable to said concentrate fluid circuit at said second location by said second connection means.

74. The system of claim 73 wherein said source of water comprises a reservoir for containing water.

75. The system of claim 74 wherein said concentrate fluid circuit includes second and third fluid conducting means, said second fluid conducting means including said first connecting means therein and communicating with said reservoir and with a first mixing point in said first fluid conducting means intermediate said first and second ends, and said third fluid conducting means containing said second connection means therein and communicating with said reservoir and with a second mixing point in said first fluid conducting means intermediate said first and second ends, said first and second mixing points being spaced from one another in said first fluid conducting means, said second fluid conducting means introducing water from said reservoir into said first vessel to produce a first concentrate fluid containing dissolved first concentrate in water and conducting said first concentrate fluid from said first vessel into said first fluid conducting means at said first mixing point to be mixed with fluid being conducted through said first fluid conducting means, and said third fluid conducting means introducing water from said reservoir into said second vessel to produce a second concentrate fluid containing dissolved second concentrate in water and conducting said second concentrate fluid from said second vessel into said first fluid conducting means at said second mixing point to be mixed with fluid being conducted through said first fluid conducting means, to thereby produce a prepared solution in said first fluid conducting means downstream of said first and second mixing points for delivery to said second end of said first fluid conducting means, said prepared solution being comprised of said first concentrate fluid and said second concentrate fluid mixed with water withdrawn from said reservoir through said first fluid conducting means.

76. The system of claim 75 wherein said first vessel has a first configuration and said second vessel has a second different configuration; and wherein said first connection means comprises a first holder configured to hold a vessel having said first configuration and said second connection means comprises a second holder configured to hold a vessel having said second configuration.

77. The system of claim 76 wherein said second fluid conducting means comprises a first fluid line which communicates with said reservoir and with an inlet to said first vessel and a second fluid line which communicates with an outlet of said first vessel and said first fluid conducting means at said first mixing point, and wherein said third fluid conducting means comprises a third fluid line which communicates with said reservoir and an inlet to said second vessel, and a fourth fluid line which communicates with an outlet of said second vessel and said first fluid conducting means at said second mixing point.

78. The system of claim 77 wherein said inlets of said first and second vessels are at the top of said vessels and said outlets of said first and second vessels are at the bottom of said vessels so that water is conducted through each of said vessels from the top thereof to the bottom thereof to thereby maintain relatively constant concentration levels of dissolved powder concentrate in said second and fourth fluid lines, respectively.

79. The system of claim 77 wherein said first holder includes an inlet connector and an outlet connector which communicate with said inlet and said outlet, respectively, of said first vessel when said first vessel is held by said first holder; wherein said second holder includes an inlet connector and an outlet connector which communicate with said inlet and said outlet, respectively, or said second vessel when said second vessel is held by said second holder; and wherein said first and second fluid lines are connected to said inlet connector and said outlet connector, respectively, of said first holder, and said third fluid and fourth fluid lines are connected to said inlet connector and said outlet connector, respectively, of said second holder.

80. The system of claim 75 further including a source of liquid concentrate and means for introducing said liquid concentrate into said first fluid conducting means at a third mixing point in said first fluid conducting means intermediate said first and second ends to be mixed with fluid being conducted through said first fluid conducting means, whereby said prepared solution is comprised of said first concentrate fluid, said second concentrate fluid and said liquid concentrate mixed with water withdrawn from said reservoir through said first fluid conducting means.

81. The system of claim 74 wherein said first vessel contains a bicarbonate material in powder form and said second vessel contains a salt material in powder form.

82. The system of calim 74, further including means for priming said system, said means for priming including valve means in said concentrate fluid circuit downstream of each of said first and second vessels and a priming fluid line connected to said valve means and to said first fliud conducting means intermediate said reservoir and the location said concentrate fluid circuit communicates with said first fluid conducting means, said valve means being operative to open said priming lines to communication with said concentrate fluid circuit for priming said system and operative to close communication between said priming line and said concentrate fluid circuit after said system has been primed.

83. The system of claim 74 further including means for disinfection of said system, said means for disinfection including a source of disinfecting solution and disinfecting fluid lines for interconnecting said first fluid conducting means and said concentrate fluid circuit in a manner to conduct disinfecting solution from said source of disinfecting solution through said first fluid conducting means and said concentrate fluid circuit.

84. The system of claim 73 wherein said first and second vessels each comprise a self-contained cartridge containing a quantity of concentrate in powder form therein which is suitable for one treatment procedure.

85. The system of claim 84 wherein each of said cartridges comprises a closed vessel having penetrable membranes at an inlet and an outlet of said closed vessel, and wherein said first connection means is connected to said first vessel through said penetrable membranes and said second connection means is connected to said second vessel through said penetrable membranes.

86. The system of claim 85 wherein each of said first and second vessels comprises a self-contained cartridge containing a quantity of concentrate in powder form therein which is suitable for one treatment procedure.

87. The system of claim 86 wherein said first cartridge contains a bicarbonate material in powder form and said second cartridge contains a salt material in powder form.

88. The system of claim 37 wherein the quantity of bicarbonate material in said first cartridge is on the order of 400 to 900 grams, and wherein the quantity of salt material contained in said second cartridge is on the order of 1,000 to 3,000 grams.

89. The system of claim 88 wherein said bicarbonate material comprises sodium bicarbonate material and said salt material comprises sodium chloride material.

90. The system of claim 84 wherein the contents of said cartridges are internally sterilized.

91. A system for preparing a fluid for a medical procedure by mixing of at least one concentrate in powder form with water, said system comprising:
a source of water;
a vessel for containing a concentrate in powder form, said vessel including an inlet at the top thereof and an outlet at the bottom thereof;
first fluid conducting means having a first end communicating with said source of water for withdrawing water from said source of water, and a second end for delivering a prepared solution;

second fluid conducting means communicating with said source of water and with said inlet of said vessel for introducing water from said source of water into the top of said vessel to produce a concentrate fluid containing dissolved powder concentrate in water; and third fluid conducting means communicating with said outlet of said vessel and with a mixing point in said first fluid conducting means intermediate said first and second ends for conducting said concentrate fluid from the bottom of said vessel into said first fluid conducting means to be mixed with fluid being conducted through said first fluid conducting means to thereby produce a prepared solution in said first fluid conducting means for delivery to said second end of said first fluid conducting means, whereby water is conducted through said vessel from the top thereof to the bottom thereof to thereby maintain a relatively constant concentration level of dissolved powder concentrate in said third fluid conducting means.

92. The system of claim 91 wherein said vessel includes a vent opening therein arranged at the top of said vessel.

93. The system of claim 92 futher including a fluid line communicating with said vent opening in said vessel and having shut-off means arranged therein operative to prevent the flow of liquid from said vessel through said fluid line.

94. The system of claim 93 wherein said flow regulating means comprises a suction pump arranged in said third fluid conducting means and wherein said fluid line communicates with said third fluid conducting means upstream of said suction pump.

95. The system of claim 93 wherein said first fluid conducting means includes a suction pump arranged therein for withdrawing water from said source of water, and wherein said fluid line communicates with said first fluid conducting means upstream of said suction pump.

96. The system of claim 93 wherein said shut-off means comprises a hydrophobic filter arranged in said fluid line.

97. The system of claim 93 wherein said shut-off means comprises a housing arranged in said fluid line and having an expansible body provided therein adapted to expand upon liquid being drawn into said housing to prevent the further flow of fluid through said housing.

98. The system of claim 93 wherein said shut-off means comprises an adjustable throttling device in said fluid line adapted to be closed after deaeration of said vessel.

99. The system of claim 91 wherein said vessel contains a concentrate in powder form having a particle size which is greater than 100 microns.

100. The system of clain 91 wherein said vessel comprises a self-contained cartridge containing a quantity of concentrate in powder form therein which is suitable for one treatment procedure.

101. The system of claim 100 wherein said cartridge comprises a closed vessel having penetrable membranes at said inlet and said outlet thereof, and wherein said second and third fluid conducting means communicate with said inlet and said outlet respectively of said closed vessel through said penetrable membranes.

102. The system of claim 101 further including connecting devices for connecting said second and third fluid conducting means to said cartridge vessel, said connecting devices each having a first end for penetrating one of said penetrable membranes and a second end to which one of said fluid conducting means is connected.

103. The system of claim 102 further including a holder for holding said vessel and wherein said connecting devices are mounted to said holder.

104. The system of claim 100 wherein the contents of said cartridge are internally sterilized.

105. The system of claim 100 wherein said cartridge contains a bicarbonate material in powder form, the quantity of said bicarbonate material in said cartridge being on the order of 400 to 900 grams.

106. The system of claim 100 wherein said cartridge contains a salt material in powder form, the quantity of salt material contained in said cartridge being on the other of 1,000 to 3,000 grams.

107. The system of claim 91 wherein said source of water comprises a reservoir for containing water.

108. A system for preparing a fluid for a medical procedure by mixing of at least one concentrate in powder form with water, said system comprising:

a vessel for containing a concentrate in powder form;

first fluid conducting means having a first end for communicating with a source of water to withdraw water into said first fluid conducting means and a second end for delivering a prepared solution;

second fluid conducting means having a first end for communicating with a source of water and a second end communicating with an inlet of said vessel for introducing water into said vessel to produce a concentrate fluid concentrate dissolved powder concentrate in water;

third fluid conducting means communicating with an outlet of said vessel and with a mixing point in said first fluid conducting means intermediate said first and second ends for conducting said concentrate fluid form said vessel into said first fluid conducting means to be mixed with fluid being conducted through said first fluid conducting means to thereby produce a prepared solution in said first fluid conducting means for delivery to said second end of said first fluid conducting means;

measuring means in said first fluid conducting means downstream of said mixing point for measuring the composition of the prepared solution obtained by mixing of said concentrate fluid and water in said first fluid conducting means; and flow regulating means in said third fluid conducting means responsive to said measuring means for controlling the flow of said concentrate fluid from said vessel.

109. The system of claim 108 further including a common source of water for said first and second fluid conducting means, said first ends of said first fluid conducting means and said second fluid conducting means each communicating with said common source of water.

110. The system of claim 109 wherein said common source of water comprises a reservoir for containing water.

* * * * *

UNITED STATES PATENT AND TRADEMARK OFFICE
CERTIFICATE OF CORRECTION

PATENT NO. : 4,784,495
DATED : November 15, 1988
INVENTOR(S) : Jonsson et al.

It is certified that error appears in the above-identified patent and that said Letters Patent is hereby corrected as shown below:

Column 5, line 41, delete "light" and insert therefor --liquid--.

Column 6, line 56, "referenc" should read --reference--.

Column 7, line 6, delete "by" and insert therefor --any--.

Column 8, line 53, delete "control" and insert therefor --conduit--.

Column 10, line 22, "meters" should read --meter--;
line 45, delete "upon" and insert therefor --open--;
line 61, "adn" should read --and--.

Column 11, line 9, "dearearato" should read --deaerator--;
line 14, "connectd" should read --connected--;
line 47, delete "use";
line 49, "outlets" should read --outlet--.

Column 12, line 57, "medicl" should read --medical--.

Column 13, line 6, "cartridge" should read --cartridges--;
line 18, "bicarbonater" should read --bicarbonate--;
line 32, "fluid" should read --fluids--.

Column 14, line 16, "vavles" should read --valves--;
line 24, "bibarbonate should read --bicarbonate--;
line 31, delete "1,00" and insert therefor --1,000--.

UNITED STATES PATENT AND TRADEMARK OFFICE
CERTIFICATE OF CORRECTION

PATENT NO. : 4,784,495

DATED : November 15, 1988

INVENTOR(S) : Jonsson et al.

It is certified that error appears in the above-identified patent and that said Letters Patent is hereby corrected as shown below:

Column 15, line 2, "cartridge" should read --cartridges--;
          line 22, "cartridge" should read --cartridges--;
          line 43, delete "is" and insert therefor --it--.

Column 16, line 16, delete "wate" and insert therefor --water--;
          line 26, delete "circuit" and insert therefor --conduit--.

Column 17, line 4, "adatped" should read --adapted--;
          line 22, delete "of" and insert therefor --or--.

Column 18, line 40, delete "containing" and insert therefor --conducting--;
          line 59, delete "fluid" and insert therefor --first--.

Column 19, line 4, "communicatig" should read --communicating--;
          line 52, delete "controlling" and insert therefor --connecting--.

Column 22, line 62, delete "containing" and insert therefor --conducting--.

Column 23, line 17, delete "secod" and insert therefor --second--;
          line 32, after "second", insert --ends and spaced from said first and second--;
          line 61, after "interconnecting", insert --said first, second, third and fourth fluid conducting--.

UNITED STATES PATENT AND TRADEMARK OFFICE
CERTIFICATE OF CORRECTION

PATENT NO. : 4,784,495

DATED : November 15, 1988

INVENTOR(S) : Jonsson et al.

It is certified that error appears in the above-identified patent and that said Letters Patent is hereby corrected as shown below:

Column 24, line 19, "throough" should read --through--.

Column 25, line 52, "communicates" should read --communicate--;
         line 57, after "third", delete "fluid".

Column 26, line 48, delete "37" and insert therefor --87--.

Column 28, line 20, delete "other" and insert therefor --order--;
         line 36, delete "concentrate" (second occurrence) and insert therefor --containing--;
         line 42, delete "form" and insert therefor --from--.

Signed and Sealed this

Twenty-third Day of May, 1989

Attest:

DONALD J. QUIGG

Attesting Officer

Commissioner of Patents and Trademarks